United States Patent [19]

Kuzuhara et al.

[11] Patent Number: 5,144,018

[45] Date of Patent: Sep. 1, 1992

[54] 2',3'-DIDEOXY-ADENOSINE DERIVATIVES

[75] Inventors: Hiroyoshi Kuzuhara; Masajiro Kawana, both of Wako; Noritsugu Yamasaki, Niiza; Masahiro Nishikawa, Kamifukuoka, all of Japan

[73] Assignee: Rikagaku Kenkyusho, Wako, Japan

[21] Appl. No.: 295,205

[22] PCT Filed: Apr. 22, 1988

[86] PCT No.: PCT/JP88/00393

§ 371 Date: Dec. 23, 1988

§ 102(e) Date: Dec. 23, 1988

[87] PCT Pub. No.: WO88/08427

PCT Pub. Date: Nov. 3, 1988

[30] Foreign Application Priority Data

Apr. 23, 1987 [JP] Japan .............................. 62-100903
Jul. 10, 1987 [JP] Japan .............................. 62-172721

[51] Int. Cl.[5] ..................... C07H 19/16; A61K 47/26
[52] U.S. Cl. ...................................................... 536/26
[58] Field of Search ............... 536/23, 24, 26; 514/45, 514/49, 46

[56] References Cited

U.S. PATENT DOCUMENTS 3,658,787  4/1972  Russell et al. ........................ 536/26
4,788,181  11/1988  Driscoll et al. ...................... 514/49
4,921,950  5/1990  Wilson ................................. 536/23

FOREIGN PATENT DOCUMENTS 1620047  3/1970  Fed. Rep. of Germany .
43-11458  5/1968  Japan .
61-280500  12/1986  Japan .

OTHER PUBLICATIONS

Tetrahedron, vol. 40. No. 1, 1984, pp. 125-135, Pergamon Press, Oxford, GB; F. Hansske et al.: "2' and 3'-ketonucleosides and their Arabino and Xylo reduction products"* Abstract; p. 126; compounds 4-9*.
Tetrahedron Letters, vol. 28, No. 35, 1987, pp. 4075-4078, Pergamon Journals Ltd., Oxford, GB; M. Kawana et al.: "The facile synthesis of 2'-azido-2',3' dideoxyadenosine. Preparative applications of the deoxygenative [1,2]-hydride shift and beta-elimination rections of sulfonates with Mg(OMe)2-NaBH4".
Journal of American Chemical Society, vol. 105, No. 22, Nov. 2, 1983, pp. 6736-6737, Am. Chemical Society; F. Hansske et al.: "A deoxygenative [1,2]-hydride shift rearrangement converting cyclic cis-diol monotosylates to inverted secondary alcohols".
Antiviral Research, vol. 6, No. 17, 1986, pp. 103-112, Elsevier Science Publishers B.V. (Biomedical Div); A. Widell et al.: "Influence of twenty potentially antiviral substances on invitro multiplication of hepatitis A virus".
Chemical Abstracts, vol. 108, No. 1, Jan. 4, 1988, p. 14, abstract No. 119v, Columbus, Ohio, US; V. E. Marquez et al.: "2'3'-Dideoxy-2'-fluoro-ara-A. An acid stable purine nucleoside active against human immunodeficiency virus (HIV)":, & Biochem. Pharmacol, 1987, 36(17), 2719-2722.
Chemical Abstract, vol. 105, No. 17, Oct. 27, 1986, p. 72, abstract No. 146227n, Columbus, Ohio, US; & JP-A-61 103 831 (Yamasa Shoyu Co., Ltd) May 22, 1986.
Chemical Abstracts, vol. 89, No. 1, 1978, p. 560, Abstract No. 6487y, Columbus, Ohio, US; H. Guglielmi et al.; "Imidazole nucleosides. III. Nucleosides of 4(5)-aminoimidazole-5(4)-carboxamide", & Hoppe-Seyler's Z. Physiol Chem. 1977, 358(11), 1463-68 Abstract.
Chemical Abstracts Formula Index, 10th Collective Index, P 3842F, C9H12N4O6, 1H-imidazole-5-carboxamide, 1H-imidazole-5-carboxamide, 1-(3-deoxy-beta-D-erythro-pentofuranosyl)-4-nitro-, p. 3929f, C9H14N4O4, 1H-imidazole-5-carboxamide, 4-amino--1-(3-deoxy-beta-D-erythro-pentofuranosyl).
Chemical Abstract. Feb. 5, 1973, Kelvin Ogilvie et al., "Anhydronucleosides VI. Synthesis of 8, 3'-Thioanhydroguanosine", 30127Z.
Barton et al., J. Chem. Soc. Perkin Transacations. I, pp. 1574-1585 (1975).
Chemical Abstracts 107:176403a. Herdewijn et al. J. Med. Chem. 30(11):2131-2137, 1987.

Primary Examiner—John W. Rollins
Assistant Examiner—Gary L. Kunz
Attorney, Agent, or Firm—Oblon, Spivak, McClelland, Maier & Neustadt

[57] ABSTRACT

The antiviral agent 2',3'-dideoxy-2'-azido-adenosine, a 5'-O- and N6- dimethoxytrityl precursor, and a synthetic intermediate, 2',3'-dideoxy-2'-iodo-adenosinie are disclosed.

3 Claims, No Drawings

2',3'-DIDEOXY-ADENOSINE DERIVATIVES

FIELD OF THE INVENTION

The present invention relates to novel intermediates useful for synthesizing various dideoxynucleoside derivatives, synthetic processes thereof, and novel dideoxynucleoside derivatives which may be synthesized from these intermediates and may be used as effective antiviral agent.

PRIOR ART

Dideoxynucleosides have now been paid attention as an effective antiviral agent for AIDS virus (HTLV III) which is a kind of retrovirus. Effectiveness of azidothymidine, dideoxycytidine, dideoxyadenosine, etc. has hitherto been confirmed, and researches on other dideoxynucleoside derivatives are also proceeded with (Inhibition of the in vitro infectivity and cytopathic effect of human T-lymphotrophic virus type III/lymphadenopathy-associated virus (HTLV-III/LAV) by 2',3'-dideoxynucleosides; and Hiroaki Mitsuya and Samuel Broder, Proc. Natl. Acad. Sci., USA vol. 83, pp. 1911–1915, March 1986, Medical Sciences).

2',3'-Dideoxyadenosine, 2',3'-dideoxyinosine, 2',3'-dideoxyguanosine and 2',3'-dideoxycytidine are sold by BIOCHEMICAL CO. in USA. These compounds are prepared using a conventional method for preparing 2',3'-dideoxycytidine (Horwitz et al., J. Org. Chem., 32(3), 817–818 (1967)) or a conventional method for preparing 2',3'-dideoxyguanosine (Prisbe et al., Synth. Commun. 1985, 15(5), 401–409).

European Patent Publication No. 206497A discloses the use of 2',3'-dideoxyinosine as an antiviral agent.

Further, the aforementioned article of Hiroaki Mitsuya et al., and Japanese Patent Unexamined Published Application No. 61-280500 disclose the use of various 2',3'-dideoxynucleosides and their derivatives as an antiviral agent, particularly against AIDS virus.

As for a synthetic method of nucleoside intermediates useful for synthesizing various dideoxynucleoside derivatives, there are prior researches by M. J. Robins, Nyilas, Chattopadhyaya, Reese, Sasaki and others. However, these synthetic methods are not fully satisfactory for industrial synthesis of dideoxynucleoside derivatives from the reason that steps required for the synthesis are long, complicated steps including an oxidation reaction follow, reagents not suitable for a large scale preparation are used, etc. Literatures with respect to these synthetic methods are enumerated below.

1) M. J. Robins et al., J. Org. Chem. 39, 2564 (1974).
2) F. Hansske and M. J. Robins, Tetrahedron Lett., 26, 4295 (1985).
3) F. Hansske, D. Madej, and M. J. Robins, Tetrahedron, 40, 125 (1984).
4) F. Hansske and M. J. Robins, J. A. Chem. Soc., 105, 6736 (1983).
5) A. Nyilas and J. Chattopadhyaya, Synthesis., 1986, 196.
6) H. Bazin and J. Chattopadhyaya, Synthesis, 1985, 1108.
7) D. G. Norman and C. B. Reese, Synthesis, 1983, 304.
8) T. Sasaki, K. Minamoto and S. Tanizawa, J. Org. Chem. 38, 2896 (1973).

Among dideoxynucleoside derivatives, one of which is now practically used as a AIDS therapeutic agent is azidothymidine. However, azidothymidine brings about strong side effects and has only an inadequate AIDS virus growth-inhibiting effect. Therefore, researches on various dideoxynucleoside derivatives must successively be proceeded with.

OBJECTS OF THE INVENTION

An object of the present invention is to provide novel dideoxynucleoside derivatives which are effective as antiviral agents.

Another object of the present invention is to provide novel nucleoside derivatives which are usable as intermediates useful for synthesis of various dideoxynucleoside derivatives.

Further object of the present invention is to provide simple synthetic methods suitable for a large scale synthesis of the above intermediates.

DESCRIPTION OF THE INVENTION

The present invention relates to nucleoside derivatives represented by the following general formula I :

wherein B is a purine base residue optionally having a protective group, a pyrimidine base residue optionally having a protective group or a imidazolyl group optionally having a protective group; $R^1$ and $R^3$ are a PivO- group, a TsO- group, a DMTrO- group or a benzoyl group; $R^2$ is a MsO- group, a TflO-group or a TsO- group.

Further, the present invention relates to nucleoside derivatives represented by the following general formula II :

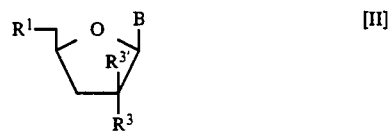

wherein B is a purine base residue optionally having a protective group, a pyrimidine base residue optionally having a protective group or a imidazolyl group optionally having a protective group; $R^1$ is $OR^4$ wherein $R^4$ is a protective group or a hydrogen atom; $R^3$ is a TsO- group, a MsO- group, a TflO-group, a PivO- group, a benzoyl group, a hydroxyl group, a mercapto group, an alkylmercapto group, an arylmercapto group, an azido group, an isothiocyanato group, a halogen atom or a hydrogen atom; $R_3'$ is a MsO- group, a TsO- group, a

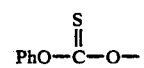

group, a

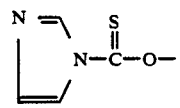

group, a hydroxyl group or hydrogen atom; provided that only one of $R^3$ and $R^{3'}$ is always a hydrogen atom; and when B is a cytosine residue having no protective group, at least one of $R^1$ and $R^{3'}$ is other than a hydroxyl group and $R^3$ is not an azido group; further, when B is an adenine residue having no protective group, at least one of $R^1$ and $R^{3'}$ is other than a hydroxyl group.

Further the present invention relates to a process for synthesizing a nucleoside derivative represented by the formula [II']:

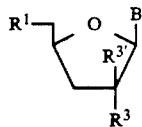

(wherein B is a purine base residue optionally having a protective group, a pyrimidine base residue optionally having a protective group or an imidazolyl group optionally having a protective group; $R_1$ is $OR^4$ wherein $R^4$ is a protective group or a hydroxyl group; $R^3$ is a hydrogen atom; and $R^{3'}$ is a hydroxyl group), which comprises treating a compound represented by the formula [I']:

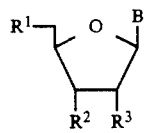

(wherein B is a purine base residue optinally having a protective group, a pyrimidine base residue optionally having a protective group or an imidazolyl group optionally having a protective group; $R^1$ and $R^3$ are a PiVO- group, a TsO- group, a DMTrO- group, a benzoyl group or a hydroxyl group; and $R^2$ is a MsO- group, a TflO- group or a TsO- group) with a base and a reducing agent.

Further the present invention relates to the process for selectively eliminating the Piv- group of B alone in the nucleoside derivatives represented by the formula [I'']:

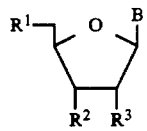

(wherein B is a purine base residue protectec by a Piv- group, a pyrimidine base residue protected by a Piv- group or an imidazolyl group protected by a Piv-group; $R^1$ and $R^3$ are a PivO- group; $R^2$ is a MsO- group, TflO- group, TsO- group, hydroxyl group or a hydrogen atom), which comprises treating nucleoside derivatives [I'']with an alkaline compound.

The present invention is explained in more detail below.

Base B in the nucleoside derivatives [I] and [II] of the present invention usually binds to the 1'-position of the ribose through a nitrogen atom in the base B, but may bind to the 1'-position of the ribose through a carbon atom therein.

In the present specification, Ms- means a mesyl group ($CH_3SO_2-$), Ts- means a tosyl group

Tfl-means a trifluoromethanesulfonyl group ($CF_3SO_2-$), Piv- means a pivaloyl group [$(CH_3)_3CO-$] and DMTr- means a 4,4'-dimethoxytrityl group.

Further, the purine base means purine derivatives having close relation to a living body. These purine derivatives are included in nucleic acids: adenines and guanines in coenzymes; uric acid, hypoxanthine, xanthine, and the like which have close relation to purine metabolism of a living body; caffeine, theophylline, theobromine and the like which are called purine alkaloids; isoguanine in a nucleoside called crotonoside; methylaminopurine synthesized when a living body is placed under a special condition; etc.

The following compounds are specifically exemplified as purine bases:

Adenine, 1-methyladenine, 2-methyladenine, N-(purine-6-yl-carbamoyl)-L-threonine, $N^6$-($\Delta^2$-isopentenyl)adenine, 2-methylthio-$N^6$-($\Delta^2$-isopentenyl)adenine, 2-hydroxyadenine, $N^6$-methyladenine, $N^6,N^6$-dimethyladenine, $N^6$-(cis-4-hydroxyisopentenyl)adenine, $N^6$-(trans-4-hydroxyisopentenyl) adenine, 2-aminoadenine, guanine, 1-methylguanine, $N^2$-methylguanine, $N^2,N^2$-dimethylguanine, 7-methylguanine, wye, wybutine, peroxywybutine, hypoxanthine, 1-methylhypoxanthine, xanthine, uric acid, 6-thiopurine, 6-chloropurine, 2,6-diaminopurine, etc.

Further, the pyrimidine base means pyrimidine derivatives having close relation to a living body. The following compounds are exemplified as main pyrimidine bases:

| | |
|---|---|
| cytosine | 4-amino-2-oxypyrimidine |
| uracil | 2,4-dioxypyrimidine |
| thymine | 2,4-dioxy-5-methylpyrimidine |
| 5-methylcytosine | 4-amino-2-oxy-5-methylpyrimidine |
| oxymethylcytosine | 4-amino-2-oxy-5-oxymethylpyrimidine |

The following compounds are specifically exemplified as other pyrimidine bases:

3-methylcytosine, $N^4$-acetylcytosine, $N^4$-methylcytosine, 2-thiocytosine, -methyluracil, 4-thiouracil, 5-hydroxyuracil, 5-hydroxymethyluracil, 5-methoxyuracil, 5-carboxymethyluracil, 2-thiothymine, 5-carboxymethyl-2-thiouracil, 5-(methoxycarbonylmethyl)-2-thiouracil, 5-(N-methylaminomethyl)-2-thiouracil, 5,6-dihydrouracil, 5,6-dihydrothymine, 5-(putrescinomethyl)uracil, S(+) 5-(4,5-dihydroxypentyl)uracil, 6-carboxyuracil, 5-fluorouracil, 5-iodouracil, etc.

Examples of the protective group contained in base B and the protective group of the oxygen atom of the $R_1$ may include a trityl group, a monomethoxytrityl group, a dimethoxytrityl group, a silicon derivative group, a pivaloyl group, an alkyl group, an acyl group, etc.

An example of nucleoside derivatives and synthetic methods thereof of the present invention is shown in schemes 1 and 2, and various embodiments of the present invention is described together therewith.

Scheme 1
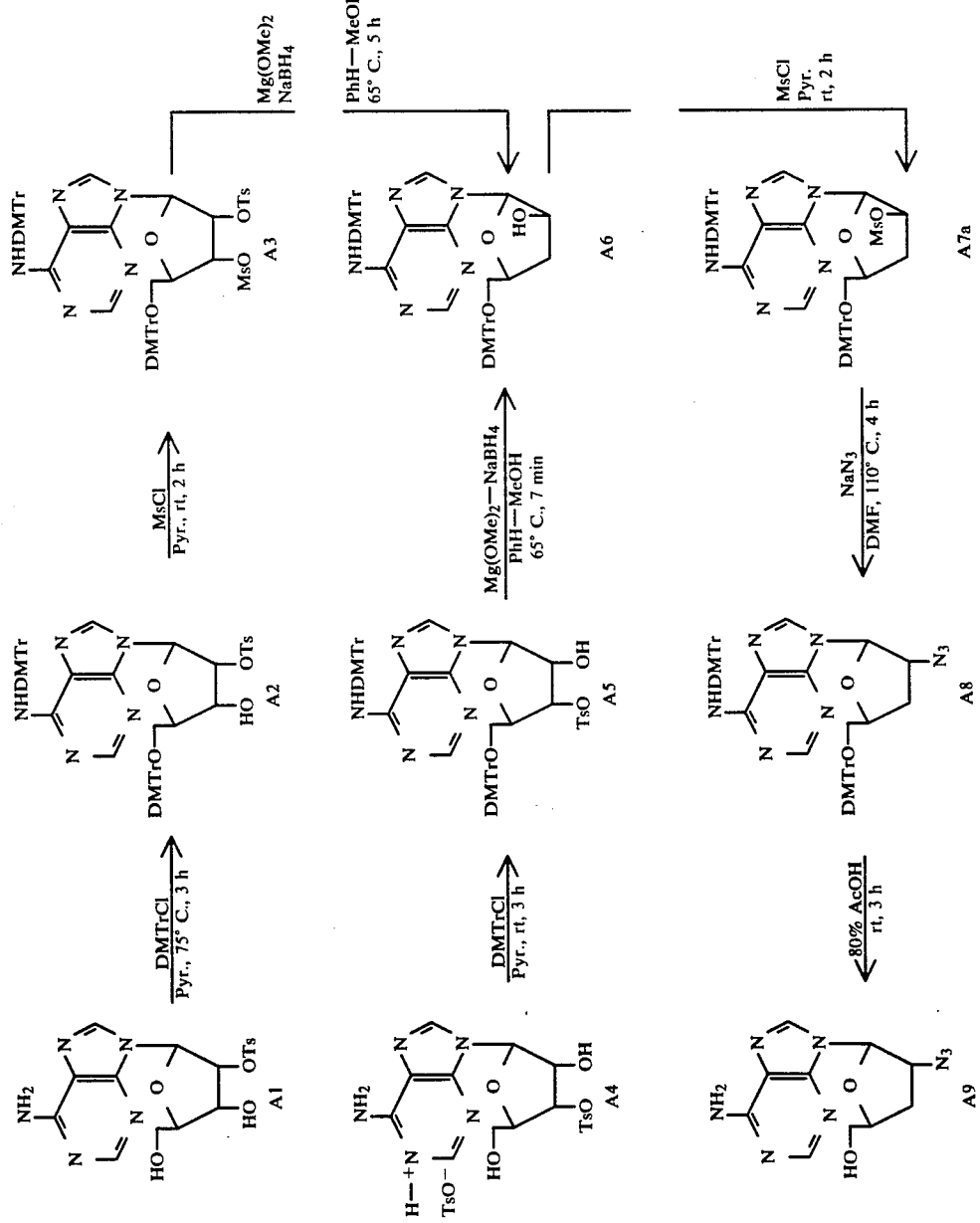

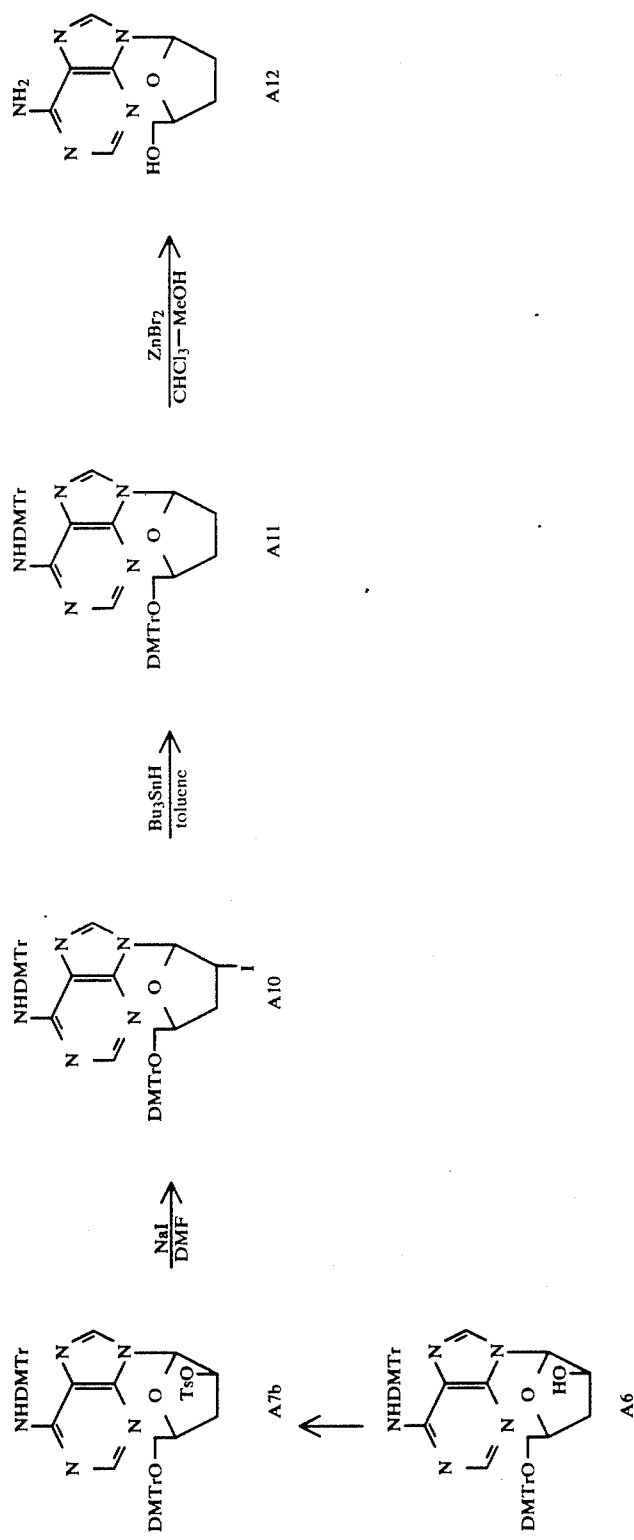

Scheme 2
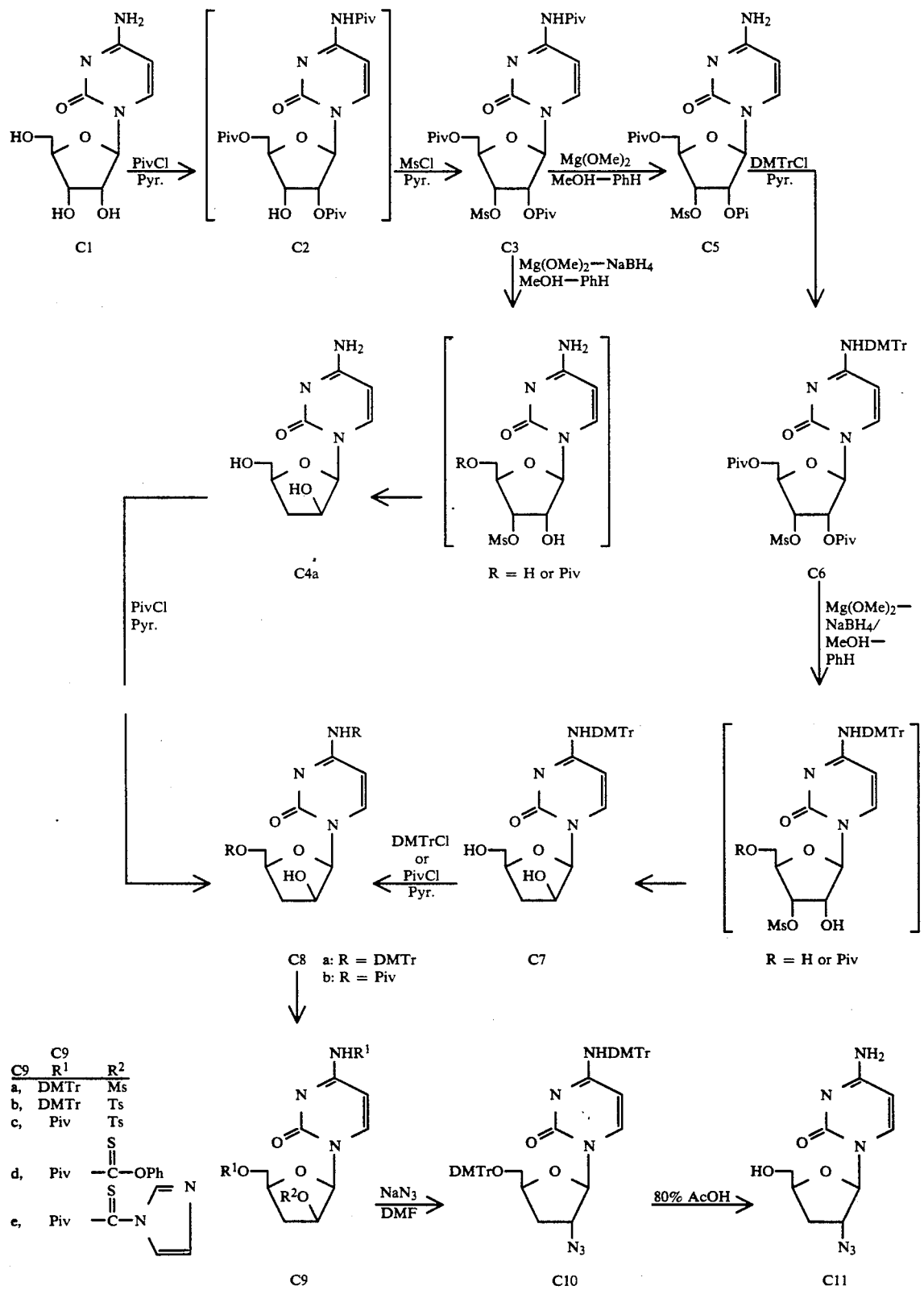

-continued
Scheme 2
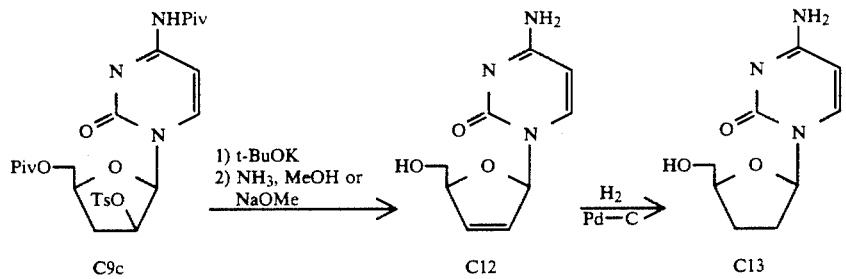
Scheme 3
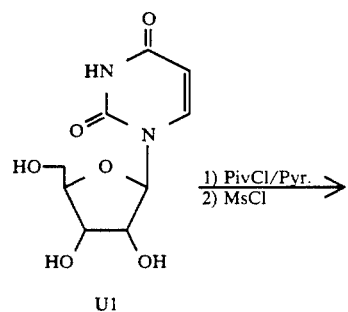
-continued
Scheme 4
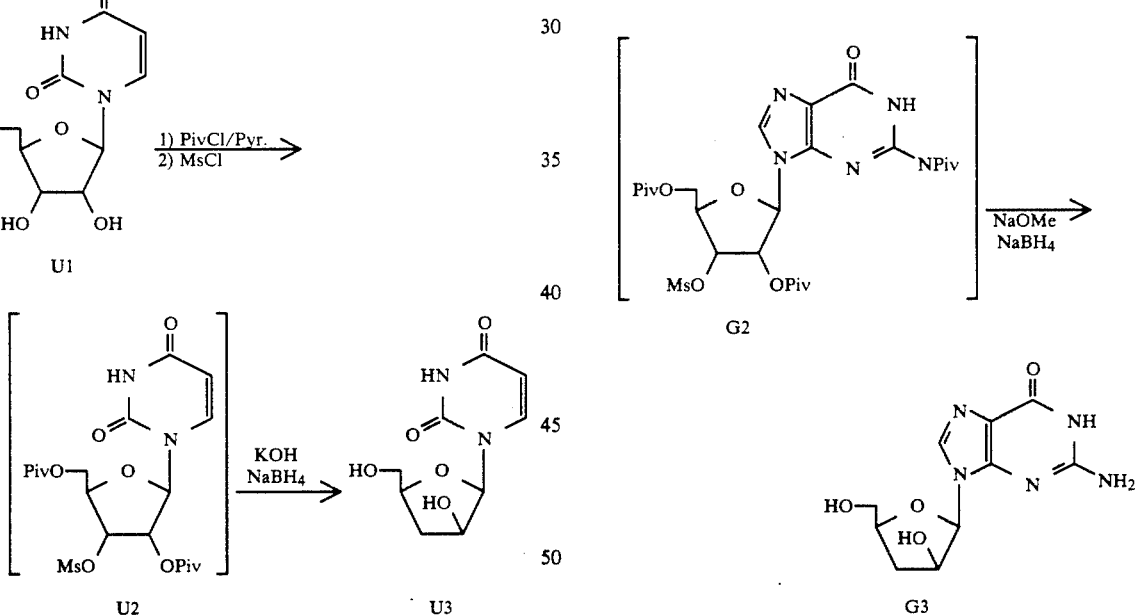
Scheme 4
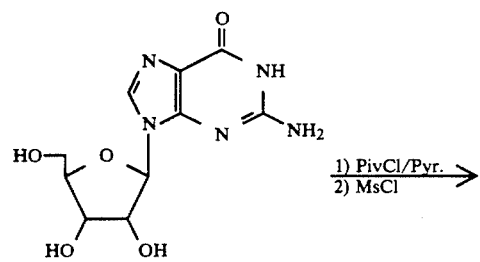
Scheme 5
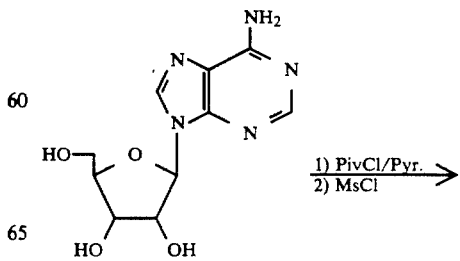

-continued
Scheme 5

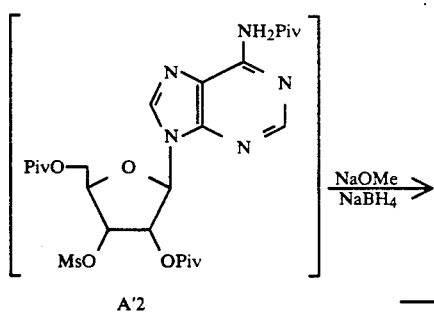

A'2

→ NaOMe/NaBH₄ →

TABLE 1-continued

| Compounds | B | Protective group of B | R¹ | R² | R³ |
|---|---|---|---|---|---|
| U2 | uracil residue | none | " | " | " |
| G2 | guanine residue | Piv— | " | " | " |
| A'2 | adenine residue | " | " | " | " |

Specific examples of nucleoside derivatives represented by the general formula [II] of the present invention are shown in Table 2.

TABLE 2

| Compounds | B | Protective group of B | R¹ | R³ | R³' |
|---|---|---|---|---|---|
| A6 | adenine residue | DMTr— | DMTrO— | H— | HO— |
| A7a | " | " | " | " | MsO— |
| A7b | " | " | " | " | TsO— |
| A8 | " | " | " | N₃— | H— |
| A9 | " | none | HO— | " | " |
| A10 | " | DMTr— | DMTrO— | I— | " |
| C7 | cytosine residue | DMTr— | HO— | H— | HO— |
| C8a | " | " | DMTrO— | " | " |
| C8b | " | Piv— | PivO— | " | " |
| C9a | " | DMTr— | DMTrO— | " | MsO— |
| C9b | " | " | " | " | TsO— |
| C9c | " | Piv— | PivO— | " | TsO— |
| C9d | " | " | " | " | PhO—C(=S)—O— |
| C9e | " | " | " | " | (morpholine)N—C(=S)—O— |
| U3 | uracil residue | none | HO— | " | HO— |
| G3 | guanine residue | " | " | " | " |
| A'3 | adenine residue | " | " | " | " |

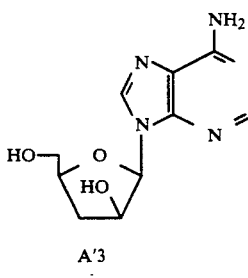

A'3

NOVEL COMPOUNDS

Specific examples of nucleoside derivatives represented by the general formula [I] of the present invention are shown in Table 1.

TABLE 1

| Compounds | B | Protective group of B | R¹ | R² | R³ |
|---|---|---|---|---|---|
| A3 | adenine residue | DMTr— | DMTrO— | MsO— | TsO— |
| C3 | cytosine residue | Piv— | PivO— | " | PivO— |
| C5 | cytosine residue | none | " | " | " |
| C6 | cytosine residue | DMTr— | " | " | " |

THE REACTION OF [I']→[II']

The reaction for synthesizing nucleoside derivatives represented by the general formula [II'] from those represented by the general formula [I'] (hereinafter referred to as [I']→[II'] reaction) is to provide nucleoside derivatives, wherein an amino group of the base residue and hydroxy groups at 2'- and 5'- positions of the ribose residue are protected and a mesyl group, a tosyl group or a trifluoromethanesulfonyl group is selectively introduced into 3'-position of the ribose residue. The resulting nucleoside derivatives are treated with a base and a reducing agent so as to effectively synthesize intermediates useful for the synthesis of dideoxynucleoside derivatives.

A mesyl group is most preferable as a functional group which is to be selectively introduced into the 3'-position of the ribose and the reaction rate thereof is very high. In order to introduce the above mentioned functional group into the 3'-position of the ribose, first of all the nucleoside is treated in a conventional manner so as to introduce selectively a protective group such as pivaloyl group into the base residue (the 2'- and 5'-positions of the ribose), then the above mentioned functional group is introduced into the 3'-position of the ribose. Thus the synthetic methods of this invention of the [I']→[II'] reaction is carried out by employing the novel nucleoside derivatives as an intermediate which is prepared by introducing the above mentioned functional group into the 3'-position of the ribose. The [I']→[II'] reaction may be carried out without isolating the compound of [I'] by continuously carrying out the processes of introducing the protective group such as pivaloyl group into the nucleoside and introducing the above mentioned functional group.

Reaction examples of the [I']→[II'] reaction and reaction conditions under which the reaction is carried out are as follows:

i) Reaction examples

| Compound | A3 → A6 |
| " | A5 → A6 |
| Compound | C3 → C4a |
| " | C6 → C7 |
| " | U2 → U3 |
| " | G2 → G3 |
| " | A'2 → A'3 | ii) Reaction conditions a) Solvent

It is preferable to use a mixed solvent containing an alcohol as the solvent, and for example, methanol, ethanol, propanol, water, benzene, toluene, hexane, chloroform, dichloroethane, N,N-dimethylformamide, dimethylsulfoxide, ether, tetrahydrofuran, dioxane, ethyl acetate, acetonitrile, etc. may be used. Further, heavy water ($D_2O$, $T_2O$), or a heavy hydrogen- of tritium-labelled alcohol may be used.

b) Reagents

As reagents, a metal alkoxide or another alkaline substance as the base, and a reducing agent may be used in an amount of 1 to 20 mole equivalents, respectively.

Preferred metal alkoxides include alkoxides such as methoxide, ethoxide, propoxide and t-butoxide of an alkali metal, an alkaline earth metal, etc., particularly magnesium, lithium, potassium, sodium or the like. Magnesium methoxide, sodium methoxide and potassium hydroxide may most advantageously be used.

Other preferable alkaline substances include sodium hydroxide, an alkylalium compound, an alkyl lithium compound, etc.

Preferred reducing agents include a metal borohydride complex containing an alkali metal or alkaline earth metal represented by sodium borohydride ($NaBH_4$), sodium cyanoborohydride, lithium cyanoborohydride, tetraalkylammonium borohydride, diborane, an aluminum-hydrogen complex represented by lithium aluminum hydride ($LiAlH_4$), an organotin hydride represented by tributyltin hydride. Further, these compound may be those heavy hydrogen- or tritium-labelled.

c) Other conditions

Reaction time is preferably 5 minutes to 20 hours, and reaction temperature is 0° to 100° C. Further, it is preferable to carry out the reaction in an inert gas such as nitrogen.

THE REACTION OF SELECTIVELY ELIMINATING THE PIV- GROUP ALONE IN THE COMPOUND [I"]

Reaction examples of the reaction for selectively eliminating the Piv- group of B alone in the nucleoside derivatives represented by the formula [I"] and reaction conditions under which the reaction is carried out are as follows:

i) Reaction example

C3→C5 ii) Reaction conditions a) Solvent

Water, methanol, ethanol, benzene, toluene, hexane, ethyl acetate, tetrahydrofuran, chloroform, ether, etc. may be used as the solvent.

b) Reagent

An alkaline compound such as a magnesium alkoxide, sodium hydroxide or potassium hydroxide is generally be used as the reagent. A magnesium alkoxide is the most preferable. When other alkaline compounds are used, temperature condition and reaction time must be controlled so that the pivaloyl group of the base alone is eliminated.

c) Other reaction conditions

Reaction time is 5 to 20 hours, and reaction temperature is 0° to 100° C.

REACTIONS IN EACH STEP SHOWN IN SCHEMES

Preferable and acceptable reaction conditions under which each of the reaction steps exemplified in schemes 1-5 is carried out are mentioned below.

Various protective groups such as trityl groups, monomethoxytrityl groups, dimethoxytrityl groups, silicon derivative groups, alkyl groups, pivaloyl groups and acyl groups may be used for the hydroxyl group at the 5'-position of ribose and the amino group of the base in each step shown in scheme 1. However, the protective groups may be present or absent except that it is required to protect the hydroxyl group at the 5'-position of the ribose in the mesylation and tosylation steps. Further, it is preferable in order to increase solubility of the nucleoside derivatives in organic solvents that either the hydroxyl group at the 5'-position of the ribose or the amino group of the base is protected.

As for synthetic methods of Compound C2 shown in scheme 2, it makes reference to Kazuo Kamaike, Fumihiko Uemura, S. Yamakage, S. Nishino, and Shunichi Ishido, "Simple synthetic procedure for 2'- and -3'-tetrahydropyranyl ribonucleoside derivatives involving regioselective acylation with acyl chlorides, and synthesis of ribonucleotide oligomers" Nucleic Acid Research, Symposium Series No. 16, 1985; Nucleosides & Nucleotides, 6, 699 (1987).

In order to synthesize Compound C3 with protection of Compound C1, it is preferable to protect the amino group of the base and the ribose 5'- and 2'-positions at the same time using pivaloyl groups as shown in scheme 2. However, acetyl groups and benzoyl groups may each also be used in place of pivaloyl groups under an adjusted reaction condition. Further, it is also possible to synthesize Compound C8a from Compound C1 through a route shown in scheme 6.

Scheme 6

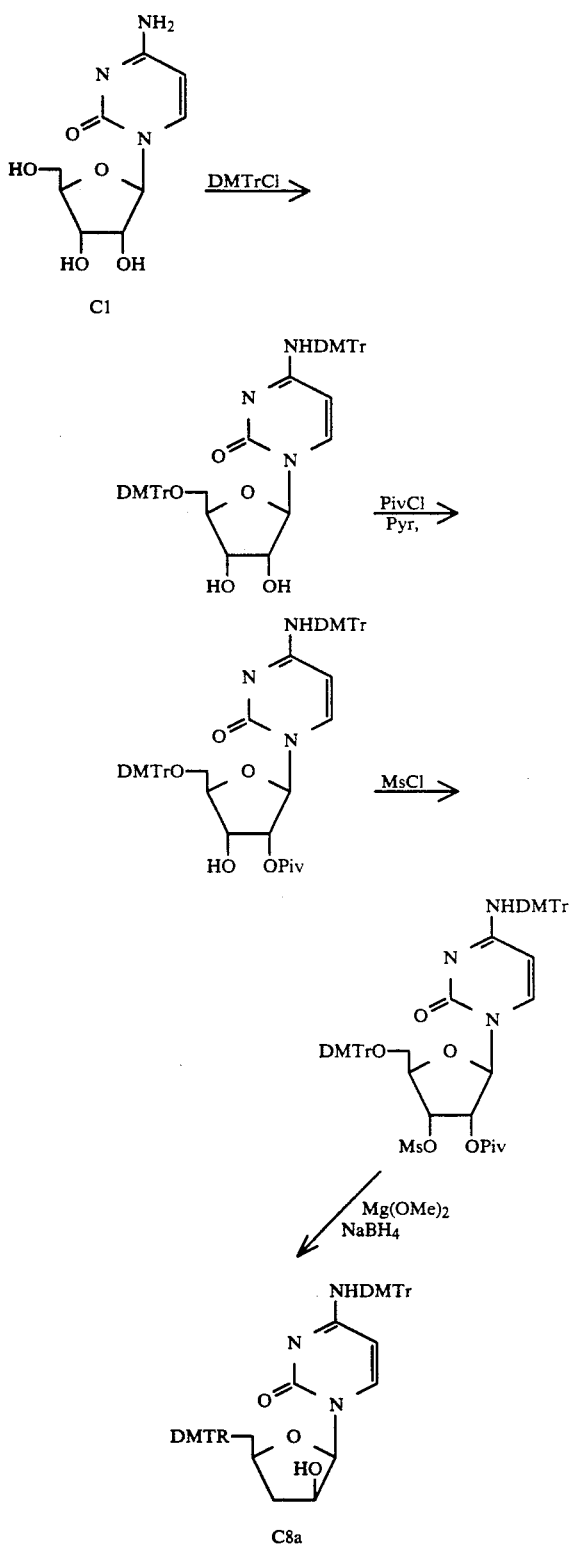

It is difficult to apply the (A3 A6)-type reaction (scheme 1) using the 2'-tosylated compound to the steps for synthesizing C4a and C7 (scheme 2) because of the existence of the carbonyl group in the base When the base does not have the carbonyl group which participates in the 2'-position or the carbonyl group of the base is protected, the 2'-tosylated compounds may be used. A method where the keto group of the base is opened and the oxygen is methylated to make an enol type may, for example, be utilized for protecting the carbonyl group of the base.

Compound C4a [1-(3-deoxy-β-D-threo-pentofuranosyl) cytosine] and biological properties thereof are disclosed in the report by W. Kreis, K. A. Watanabe, and J. J. Fox [Helv. Chem. Acta, 61, 1011 (1978)].

Compound C11 (2'-azido-2',3'-dideoxycytidine) and biological properties thereof are disclosed in the report by Shunji Izuta, Shigeru Kimura, Kenji Takenuki, and Mineo Saneyoshi, (Nucleic Acid Research, Simp. ser., No. 17, 1986, p. 154).

1) Synthesis of Compounds A1 and A4

Compound A1 and Compound A4, starting compounds disclosed in scheme 1 may be obtained by a known method, for example by tosylating the nucleoside in the route shown in the following scheme 7.

Scheme 7

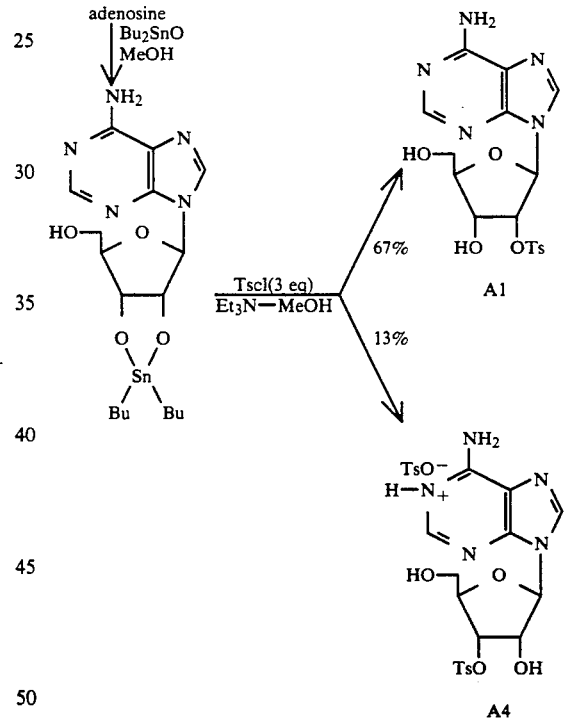

The 2'-O-tosyl compound (Compound A1) and the 3'-O-tosyl compound (Compound A4) may readily be separated by fractional crystallization. Heretofore, a method of obtaining an intermediate (corresponding to Compound A6) for synthesis of dideoxynucleoside derivatives from the 3'-O-tosyl compound (Compound A4) has been known (F. Hansske and M. J. Robins, J. Am. Chem Soc., 105, 6736 (1983)). However, in this method the large scale preparation of the 3'-O-tosyl compound (Compound A4) is tedious On the other hand, synthetic method of the invention allows the use of the 2'-O-tosyl compound in addition to the 3'-O-tosyl compound as the starting materials.

Though the starting material used in scheme 7 is adenosine, such nucleosides as specifically exemplified below may further be used in the present invention in place of adenosine: 1-methyladenosine, 2-methyladenosine, N⁶-methyladenosine, N⁶,N⁶-dimethyladenosine, 2-hydroxyadenosine, N-[(9-β-D-ribofuranosylpurin-6-yl)carbamoyl]-L-threonine, N-[(9-β-D-ribofranosyl(purin-6-yl)-N-methylcarbamoyl]threonine, N- [(9-β-D-ribofranosyl-2-methylthiopurin-6-yl)carbamoyl]threonine, N⁶-(Δ²-isopentenyl)adenosine, 2-methylthio-N⁶-(Δ²-isopentenyl)adenosine, N⁶-(cis-4-hydroxyisopentenyl)adenosine, 2-methylthio-N⁶-(cis-4-hydroxyisopentenyl)adenosine, zeatosine, cytidine, 2-thiocytidine, 3-methylcytidine, N⁴-acetylcytidine, 5-methylcytidine, guanosine, 1-methylguanosine, N²-methylguanosine, N²,N²-dimethylguanosine, N²,N²-dimethylguanosine, 7-methylguanosine, N²,N²,7-trimethylguanosine, wyosine, wybutosine, peroxywybutosine, Q nucleoside, Q*nucleoside (the compound where the hydroxyl hydrogen atom at the 5-position of the cyclopentene of Q uncleoside is replaced by a galactosyl residue depicted below).

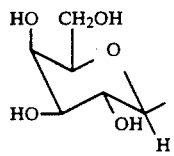

inosine, 1-methylinosine, xanthosine, uridine, 3-methyluridine, 5-methyluridine, 5-methyl-2-thiouridine, 4-thiouridine, 5-carboxymethyluridine, 5-carboxymethyl-2-thiouridine, 5-(carboxymethylaminomethyl)uridine, 5-(carboxymethylaminomethyl)-2-thiouridine, 5-(methoxycabonylmethyl)uridine, 5-(methoxycarbonylmethyl)-2-thiouridine, 5-(methylaminomethyl)-2-thioridine, 3-(3-amino-3-carboxypropyl)uridine, 5-hydroxyuridine, 5-methoxyuridine, methyl uridine-5-oxyacetate, 5-hydroxymethyluridine, dihydrouridine, 5-methyl-5,6-dihydrouridine, pseudouridine, 1-methyl-3-(3-amino-3-carboxypropyl)pseudouridine, orotidine, etc.

2) Compound A2→Compound A2

Compound A2 may be obtained by reacting Compound A1 with dimethoxytrityl chloride in a solvent such as pyridine or triethylamine, preferably at a temperature of 65° to 85° C. for 1 to 3 hours.

General reaction conditions for obtaining Compound A2 from Compound A1 are as follows.

a) Solvent

As the solvent, a solvent mainly consisting of pyridine or triethylamine is used. However, an aprotic organic solvent may be used in combination therewith. Examples of the aprotic organic solvent are benzene, toluene, hexane, chloroform, dichloroethane, dichloromethane, N',N-dimethylformamide, dimethylsulfoxide, ether, tetrahydrofuran, dioxane, ethyl acetate, acetonitrile, etc.

However, a neutral solvent is used when 3,4-dihydro-2H-pyran is used as a reagent.

b) Catalyst

As a catalyst, 4-dimethylaminopyridine, an alkali metal or alkaline earth metal alkoxide (sodium methoxide, etc.), one of various Grignard reagents (t-butylmagnesium chloride, etc.) or the like is used in an amount of 0.1 to 10 mole equivalents.

However, when the pyran is used as a reagent, benzenesulfonic acid, toluenesulfonic acid, camphorsulfonic acid, Hydrochloric acid, sulfuric acid, a strongly acidic ion exchange regin or the like is used as an acid catalyst.

c) Reagent

As a reagent, trityl chloride, monomethoxytrityl chloride, dimethoxytrityl chloride, benzyl chloride, benzyl bromide, monomethoxybenzyl chloride, monomethoxybenzyl bromide, dimethoxybenzyl chloride, dimethoxybenzyl chloride, β-methoxyethoxymethyl chloride, methoxymethyl chloride, benzoyl chloride, acetyl chloride, pivaloyl chloride, t-butyldimethylsilyl chloride, dimethylphenylsilyl chloride, 3,4-dihydro-2H-pyran or the like is used.

d) Other conditions

Reaction time is 10 minutes to 20 hours, reaction temperature is 0° to 100° C., and the reaction is carried out at normal pressure while humidity is avoided.

3) Compound A2→Compound A3

Compound A3 may be obtained by reacting Compound A2 with mesyl chloride in a solvent such as pyridine or triethylamine, preferably at room temperature for 1 to 3 hours.

General reaction conditions for obtaining Compound A3 from Compound A2 are as follows.

a) Solvent

As the solvent, a solvent mainly consisting of pyridine or triethylamine is used. However, an aprotic organic solvent may be used in combination therewith. Examples of the aprotic organic solvent are benzene, toluene, hexane, chloroform, dichloroethane, dichloromethane, N,N-dimethylformamide, dimethylsulfoxide, ether, tetrahydrofuran, dioxane, ethyl acetate, acetonitrile, etc.

b) Catalyst

As a catalyst, 4-dimethylaminopyridine, an alkali metal or alkaline earth metal alkoxide (sodium methoxide, etc.), one of various Grignard reagents (t-butylmagnesium chloride, etc.) or the like is used in an amount of 0.1 to 10 mole equivalents.

c) Reagent

As the reagent, an acid chloride, acid anhydride, acid imidazolide or the like of methanesulfonic acid, toluenesulfonic acid, trifluoromethanesulfonic acid or the like may be used.

d) Other conditions

Reaction time is 10 minutes to 20 hours, reaction temperature is 0° to 100° C., and the reaction is carried out at normal pressure while humidity is avoid.

4) Compound A3→Compound A6

Compound A6 may be obtained by reacting Compound 3 with magnesium methoxide, sodium methoxide or the like in the presence of a reducing agent such as sodium borohydride in a benzene-methanol mixed solvent at a temperature of 55° to 75° C. for 3 to 7 hours.

General reaction conditions are the same with those of the [I']→[II'] reaction.

5) Compound A4→Compound A5

Compound A5 may be obtained by reacting Compound A4 with dimethoxytrityl chloride in a solvent such as pyridine, preferably at room temperature for 2 to 4 hours.

General reaction conditions for obtaining Compound A5 form Compound A4 are the same with general reaction conditions for obtaining Compound A2 from Compound A1.

6) Compound A5→Compound A6

Compound A6 may be obtained by reacting Compound A5 with magnesium methoxide, sodium methoxide or the like in the presence of sodium borohydride or the like as a catalyst in a benzene-methanol mixed solvent, preferably at 55° to 75° C. for 5 to 10 minutes.

General reaction conditions are the same with those of the [I']→[II'] reactions.

7) Compound A6→Compound A7a

Compound A7a may be obtained by reacting Compound A6 with mesyl chloride in a solvent such as pyridine, preferably at room temperature for 1 to 3 hours.

General reaction conditions for obtaining Compound A7a are the same with general reaction conditions for obtaining Compound A3 from Compound A2.

8) Compound A7a→Compound A8

Compound A8 may be obtained by reacting Compound A7a with sodium azide in a solvent such as dimethylformamide or diethylformamide, preferably at a temperature of 100° to 120° C. for 3 to 5 hours.

General reaction conditions for obtaining Compound A8 from Compound A7a are as follows.

a) Solvent

As the solvent, a solvent mainly consisting of N,N-dimethylformamide, N,N-diethylformamide or dimethylsulfoxide is used, and solvents as exemplified below may be used in combination therewith. That is, benzene, toluene, hexane, chloroform, dichloroethane, dichloromethane, ether, tetrahydrofuran, dioxane, ethyl acetate, pyridine, acetonitrile, methanol, ethanol, propanol, water, etc. may be added.

b) Reagent

An alkali metal azide compound may be used as the reagent, and sodium azide or lithium azide is preferably used.

c) Other conditions

Preferably, reaction time is 10 minutes to 20 hours, and reaction temperature is 0° to 150° C.

9) Compound A8→Compound A9

Compound A9 may be obtained by treating Compound A8 in the presence of an acid catalyst, preferably at room temperature for 2 to 4 hours to carry out hydrolysis.

General reaction conditions for obtaining Compound A9 from Compound A8 are as follows.

a) Solvent

Water, methanol, ethanol, propanol, pyridine, N,N-dimethylfomamide, dimethylsulfoxide, benzene, toluene, hexane, chloroform, dichloroethane, dichloromethane, ether, tetrahydrofuran, dioxane, ethyl acetate, acetonitrile, etc. may be used as the solvent.

b) Catalyst

Acetic acid, formic acid, hydrochloric acid, p-toluenesulfonic acid, sulfonic acid, comphorsulfonic, acid, zinc bromide, zinc chloride, an acidic ion exchange resin, etc. may be used as the catalyst. Amount of the catalyst is 0.001 mole% to a large excessive amount.

c) Other reaction conditions

Reaction time is 5 minutes to 20 hours and reaction temperature is −20° to 100° C.

10) Compound A6→Compound A7b

Acquisition of Compound A7b from Compound A6 may be attained by tosylating $R^{3'}$ according to a known method, for example using TsCl and $Et_3N$-pyridine.

11) Compound A7b→Compound A10

The same reaction conditions as in the case of synthesis of Compound A8 from Compound A7a may be used, provided that an alkali metal iodo compound such as sodium iodide or lithium iodide, or an alkyl or aryl quaternary ammonium iodo compound such as tetra-n-butylammonium iodide is used in place of the azide compound as the reagent is used.

12) Compound A10→Compound A11

Compound A11 is synthesized by reacting Compound A10 with a reducing agent such as tributyltin hydride in a solvent such as toluene, preferably in the presence of azobisisobutyronitrile or light of a mercury lamp as catalysts at room temperature for 30 minutes to 6 hours.

General reaction conditions for obtaining Compound A11 from Compound A10 are as follows.

a) Solvent

Benzene, toluene, cyclohexane, hexane, methanol, ethanol, ethyl acetate, etc. may be used as a solvent.

b) Catalyst

As catalysts, a radical-generating agent such as azobisisobutyronitrile in an amount of 0.01 to 1 mole equivalent, light (preferably, that of a mercury lamp), etc. may be used.

c) Reducing agent

A metal borohydride complex containing an alkali metal or alkaline earth metal represented by sodium borohydride ($NaBH_4$), sodium cyanoborohydride, lithium cyanoborohydride, tetraalkylammonium borohydride, diborane, an aluminum-hydrogen complex represented by lithium aluminum hydride ($LiAlH_4$), an organotin hydride represented by tributyltin, etc. may preferably used as a reducing agent. Further, these compounds may be those heavy hydrogen- or tritium-labelled.

A reducing agent may be used preferably in an amount of 1 to 10 mole equivalent.

Other reaction conditions

Reaction time is preferably 5 minutes to 24 hours, and reaction temperature is preferably room temperature to 120° C. Further, it is preferable to degas the solvent and to carry out the reaction under an inert gas stream.

13) Compound A11→Compound A12

Compound A12 may be obtained by treating Compound A11 in the presence of an acid catalyst, preferably at room temperature for 2 to 4 hours to carry out hydrolysis.

General reaction conditions for obtaining Compound A12 from Compound A11 are the same with reaction conditions for obtaining Compound A9 from Compound A8.

14) Compound C3→Compounds C4a, C4b and C4c

A method of synthesizing Compound C4a from Compound C3 and reaction conditions thereof are the same with the method and reaction conditions for obtaining Compound A6 from Compound A3.

General reaction conditions are the same with those of the [I']→[II'] reaction.

Because of a strong hygroscopic nature and difficulty of purification thereof, Compound C4a may be crystallized in methanol as picrate (C4b) or hydrochloride (C4c).

15) Compound C3→Compound C5

Compound C5 may be obtained by reacting Compound C3 with magnesium methoxide, preferably in a methanol-benzene solvent at a temperature of 20° to 30° C. for 30 minutes to 2 hours.

General reaction conditions for obtaining Compound C5 from Compound C3 are as follows:

a) Solvent

Water, methanol, ethanol, benzene, toluene, hexane, ethyl acetate, tetrahydrofuran, chloroform, ether, etc. may be used as the solvent.

b) Reagent

An alkaline compound such as a magnesium alkoxide, sodium hydroxide or potassium hydroxide is generally be used as the reagent. A magnesium alkoxide is the most preferable. When other alkaline compounds are used, temperature condition and reaction time must be controlled so that the pivaloyl group of the base alone is eliminated.

c) Other reaction conditions

Reaction time is 5 to 20 hours, and reaction temperature is 0° to 100° C.

16) Compound C5→Compound C6

Compound C6 may be obtained by reacting Compound C5 with DMTrCl in a pyridine solvent according to a known method to protect the base.

17) Compound C6→Compound C7

The method and reaction conditions for synthesizing Compound C7 from Compound C6 are the same with the method and reaction conditions for obtaining Compound A6 from Compound A3.

General reaction conditions are the same with the [I']→[II'] reaction.

18) Compound C4a or C7→Compound C8

Compound C8a or C8b may be obtained by reacting Compound C4a or C7 with DMTrCl or PivCl in a pyridine solvent according to a known method to protect the base and the ribose 5'-position.

19) Compound C8→Compound C9

Compounds C9a to C9e may be obtained by reacting Compound C8a or C8b with mesyl chloride, tosyl chloride, phenyl chlorothionocarbonate or 1,1'-thiocarbonyldiimidazole in a solvent such as pyridine, preferably at room temperature for 1 to 3 hours.

General reaction conditions of the step for obtaining Compound C9 are the same with the general reaction conditions for obtaining Compound A3 from Compound A2.

20) Compound C9→Compound C10

The method of synthesizing Compound C10 from Compound C9 and reaction conditions therefor are the same with the method and reaction conditions for synthesizing Compound A8 from Compound A7.

21) Compound C10→Compound C11

The method and reaction conditions of synthesizing Compound C11 from Compound C10 are the same with the method and reaction conditions for synthesizing Compound A9 from Compound A8.

22) Compound C9c→Compound C12

Compound C12 may be obtained by reacting Compound C9c, preferably, with sodium methoxide in a methanol solvent at room temperature for 24 hours.

General reaction conditions for obtaining Compound C12 from Compound C9c are as follows:

a) Solvent

A sole solvent or a mixed solvent of an alcohol such as methanol, ethanol, i-propanol or t-butanol, N,N-dimethylformamide, N,N-diethylformamide and dimethylsulfoxide may preferably used as the solvent. Benzene, ethyl acetate, hexane, tetrahydrofuran, dioxine, etc. may also be used.

b) Reagent

A metal alkoxide such as sodium methoxide or potassium t-butoxide, sodium hydroxide, potassium hydroxide, an alkali metal hydride such as sodium hydride, DBN(1,5-diazabicyclo[4,3,0]-nonene-5), DBU(1,8-diazabicyclo[5,4,0]-unde-7-cene), or a metal alkylamide such as lithium diethylamide is used in an amount of 0.01 to 10 mole equivalents as the reagent.

c) Other reaction conditions

Reaction time is 10 minutes to 24 hours, reaction temperature is room temperature to 140° C., and the reaction is preferably carried out an under dry, inert gas atmosphere.

23) Compound C12→Compound C13

Compound C13 may preferably be obtained by treating Compound C12 in a methanol solvent in the presence of hydrogen gas and palladium catalysts at room temperature for 30 minutes to one hour.

General reaction conditions for obtaining Compound C13 from Compound C12 are as follows.

a) Solvent

Methanol, ethanol, i-propanol, water, etc. may be used as the solvent.

b) Catalyst

As the catalysts, a metal catalyst such as palladium, platinum, rhodium, ruthenium or nickel, may be used in an amount of 0.01 to 10 weight %.

c) Other reaction conditions

It is preferable that reaction time is 10 minutes to 24 hours, reaction temperature is 0° to 100° C. and hydrogen gas is used at 1 to 100 atoms.

24) Compound U2→U3, G2→G3, A'2→A'3

Preferable reaction conditions are the same with those of the A3→A6 reaction, and general reaction conditions are the same with those of the [I']→[II'] reaction.

THE BEST EMBODIMENT FOR CARRYING OUT THE INVENTION

The present invention is further specifically described below according to examples and reference example.

REFERENCE EXAMPLE 1

Synthesis of
$N^6,O^{5'}$-bis(4,4'-dimethoxytrityl)-2'-O-tosyladenosine
(Compound A2)

2'-O-Tosyladenosine (Compound A1) (4.21 g, 10 mmol) and 4,4'-dimethoxytrityl chloride (7.45 g, 22 mmol) were added to anhydrous pyridine (50 ml), and stirred at room temperature for 20 hours. After ice cooling, 50% aqueous pyridine was added, the mixture was extracted with chloroform, and the organic layer was washed successively with aqueous sodium bicarbonate and water, and dried over magnesium sulfate. After distillating away the chloroform, the pyridine was removed by co-evaporation with toluene, and the residue was subjected to silica gel column chromatography [eluant : toluene-ethyl acetate-triethylamine→(9:1:0.1) toluene-ethyl acetate-triethylamine-methanol (9:1:0.1:0.2)]. Fractions containing the desired substance were combined and concentrated to give Compound A2 (7.74 g, yield 75%).

PHYSICAL PROPERTIES OF COMPOUND A2

Powders (Amorphous)

| | Elementary analysis | | | |
|---|---|---|---|---|
| | C | H | N | S |
| Calculated (%) (for $C_{59}H_{55}N_5O_{10}S$) | 69.06 | 5.40 | 6.82 | 3.12 |
| Found (%) | 68.94 | 5.39 | 6.74 | 3.21 |

Specific rotations; $[\alpha]^{24}_D = -39.2°$ (c=0.5, CHCl$_3$).
UV spectrum $\lambda^{MeOH}_{max}$ 274 nm ($\epsilon$26,100).

| IR spectrum |
|---|
| (KBr) |

-continued

| 3450 | 1253 | 705 |
| --- | --- | --- |
| 2960 | 1178 | 583 |
| 1608 | 1035 | 553 cm$^{-1}$ |
| 1510 | 828 | |

$^1$H-NMR spectrum CDCl$_3$, δ

| | |
| --- | --- |
| 2.29 (3H, s, C—CH$_3$) | 4.65 (1H, m, H-3') |
| 3.31 (1H, dd, H-5') | 5.73 (1H, t, H-2') |
| 3.44 (1H, dd, H-5") | 6.07 (1H, d, H-1') |
| 3.77 (12H, s, O—CH$_3$) | 7.73 (1H, s, H-2) |
| 4.19 (1H, m, H-4') | 7.81 (1H, s, H-8) |

EXAMPLE 1

Synthesis of N$^6$,O$^{5'}$-bis(4,4'-dimethoxytrityl)-9-(3-O-mesyl-2-O-tosyl-β-D-ribofranosyl)anenine (Compound A3)

Mesyl chloride (1.45 ml, 18.6 mmol) was added to a solution of the monotosyl compound (Compound A2) (9.50 g, 9.3 mmol) in anhydrous pyridine (40 ml) at room temperature, the mixture was stirred for one hour. After cooling, 50% aqueous pyridine was added to decompose an excess of the mesyl chloride. The reaction mixture was extracted with ether, and the ether layer was washed successively with water, aqueous sodium bicarbonate and water, and dried over magnesium sulfate. After removal of the ether, the pyridine was removed under reduced pressure by co-evaporation with toluene, and the residue was subjected to silica gel column chromatography [eluant : benzene-ethyl acetate-triethylamine (95:5:1)→benzene-ethyl acetate-triethylamine-methanol (9:5:5:1:1).] The fractions containing the desired product were combined and concentrated to afford 8.35 g of Compound A3 (yield 81%). A part thereof was dissolved in dichloromethane, and the solution was dropwise added to pentane to prepare an analytical sample.

PHYSICAL PROPERTIES OF COMPOUND A3

Powders (Amorphous)

| | Elementary analysis | | | |
| --- | --- | --- | --- | --- |
| | C | H | N | S |
| Calculated (%) (for C$_{60}$H$_{57}$N$_5$O$_{12}$S$_2$.C$_5$H$_{12}$) | 66.36 | 5.91 | 5.95 | 5.45 |
| Found (%) | 66.26 | 6.01 | 5.80 | 5.41 |

Specific rotations: [α]$^{20}_D$ = −34.1° (c=0.6, CHCl$_3$).
UV spectrum λ$^{MeOH}_{max}$ 273 nm (ε27,900).

| IR spectrum (KBr) | | | |
| --- | --- | --- | --- |
| 3440 | 1470 | 1180 | 705 |
| 2980 | 1370 | 1070 | 670 |
| 1610 | 1300 | 1034 | 580 |
| 1510 | 1255 | 830 | 553 cm$^{-1}$ |

$^1$H-NMR spectrum CDCl$_3$, δ

| | |
| --- | --- |
| 2.28 (3H, s, Ts-CH$_3$) | 4.45 (1H, q, H-4') |
| 3.11 (3H, s, Ms-CH$_3$) | 5.44 (1H, dd, H-3') |
| 3.45 (1H, dd, H-5') | 5.89 (1H, dd, H-2') |
| 3.54 (1H, dd, H-5") | 6.08 (1H, d, H-1') |
| 3.78 (12H, s, O—CH$_3$) | 7.69 (1H, s, H-2) |
| | 7.78 (1H, s, H-8) |

EXAMPLE 2

Synthesis of N$^6$,O$^{5'}$-bis(4,4'-dimethoxytrityl)-9-(3-deoxy-β-D-threo-pentofuranosyl)adenine (Compound A6)

Method 1

From Compound A3

Disulfonate (Compound A3) (110 mg, 0.1 mmol) was dissolved in a mixture of benzene (1 ml) and methanol (1 ml), and magnesium methoxide (86 mg, 1 mmol) and sodium borohydride (19 mg, 0.5 mmol) were added thereto at room temperature. The mixture was stirred at 65°–70° C. under an atmosphere of dry nitrogen for 4 hours. After cooling, acetone (0.5 ml) was added to inactivate an excess of the reducing agent, and the mixture was extracted with ether containing a small amount of chloroform. The organic layer was washed successively with an aqueous ammonium chloride and water, and dried over magnesium sulfate. The organic solvent was distilled away and the residue was subjected to silica gel column chromatography eluant : benzene-ethyl acetate-triethylamine (9:1:0.1) benzene-ethyl acetate-triethylamine-methanol (9:1:0.1:0.1)]. Fractions containing the desired substance were concentrated to give Compound A6 (63 mg, yield 73%).

Method 2

From Compound A5

In a manner similar to Method 1, monotosyl compound (Compound A5) (102 mg, 0.1 mmol) was treated with magnesium methoxide (1 mmol)-sodium borohydride (0.5 mmol) at 65° C. for 7 minutes, and Compound A6 was obtained after the column chromatography (85 mg, yield 99%).

PHYSICAL PROPERTIES OF COMPOUND A6

Powders (Amorphous)

| | Elementary analysis | | |
| --- | --- | --- | --- |
| | C | H | N |
| Calculated (%) (for C$_{52}$H$_{49}$N$_5$O$_7$.0.2H$_2$O) | 72.66 | 5.79 | 8.15 |
| Found (%) | 72.84 | 6.08 | 7.87 |

Specific rotations: [α]$_D^{22}$ = +9.2° (c=0.9, CHCl$_3$).
UV spectrum λ$_{max}^{MeOH}$274 nm (ε30,000).

| IR spectrum (KBr) | | |
| --- | --- | --- |
| 3440 | 1254 | 705 |
| 2970 | 1180 | 585 |
| 1610 | 1037 | cm$^{-1}$ |
| 1510 | 830 | |

$^1$H-NMR spectrum CDCl$_3$, δ

| | |
| --- | --- |
| 2.15 (1H, m, H-3') | 2.47 (1H, m, H-3") |
| 3.19 (1H, dd, H-5') | 4.53 (2H, br s, H-2') and OH) |
| 3.56 (1H, dd, H-5") | 6.06 (1H, d, H-1') |
| 3.78 (12H, s, O—CH$_3$) | 8.02 (1H, s, H-2) |
| 4.34 (1H, m, H-4') | 8.24 (1H, s, H-8) |

EXAMPLE 3

Synthesis of
N$^6$,O$^{5'}$-bis(4,4'-dimethoxytrityl)-9-(3-deoxy-2-O-mesyl-
β-D-thereo-pentofuranosyl)adenine (Compound A7)

A solution of N$^6$,O$^{5'}$-bis(4,4'-dimethoxytrityl)-9-(3-deoxy-β-D-threo-pentofuranosyl)adenine (Compound A6) (544 mg, 0.64 mmol) in anhydrous pyridine (4 ml) was cooled with ice water, methanesulfonyl chloride (0.2 ml, 2.6 mmol) was added, and the mixture was stirred at room temperature for 5 hours. After cooling, 50% aqueous pyridine was added to decompose an excess of the reagent, and the mixture was diluted with chloroform. The organic layer was washed successively with water, aqueous sodium bicarbonate and water and dried over magnesium sulfate. The organic solvents were removed under reduced pressure. The residue was subjected to silica gel column chromatography [eluant : chloroform-methanol-triethylamine (99:1:1) ] to provide 556 mg of the mesylate compound (Compound A7) (yield 93%). A part of the product was dissolved in dichloromethane and the solution was dropwise added to pentane to form a precipitate, which was then used as an analytical sample.

PHYSICAL PROPERTIES OF COMPOUND A7

Powders (Amorphous)

| Elementary analysis | C | H | N | S |
|---|---|---|---|---|
| Calculated (%) (for C$_{53}$H$_{51}$N$_5$O$_9$S.0.7C$_5$H$_{12}$) | 68.93 | 6.08 | 7.11 | 3.26 |
| Found (%) | 68.89 | 6.11 | 6.94 | 3.32 |

Specific rotations: $[\alpha]_D^{22} = +8.2°$ (c=0.9, CHCl$_3$).
UV spectrum $\lambda_{max}^{MeOH}$274 nm (ε29,400).

| IR spectrum (KBr) | | |
|---|---|---|
| 3420 | 1367 | 824 |
| 2950 | 1250 | 750 |
| 1600 | 1173 | 700 |
| 1505 | 1030 | 580 cm$^{-1}$ |

| $^1$H-NMR spectrum CDCl$_3$, δ | |
|---|---|
| 2.47 (1H, m, H-3') | 3.78 and 3.79 (12H, s, O—CH$_3$) |
| 2.62 (1H, m, H-3") | 4.34 (1H, m, H-4') |
| 2.52 (3H, s, C—CH$_3$) | 5.32 (1H, m, H-2') |
| 3.38 (1H, dd, H-5') | 6.34 (1H, d, H-1') |
| 3.44 (1H, dd, H-5") | 8.00 (1H, s, H-2) |
| | 8.02 (1H, s, H-8) |

EXAMPLE 4

Synthesis of
N$^6$,O$^{5'}$-bis(4,4'-dimethoxytrityl)-9-(3-deoxy-2-0-tosyl-
β-D-threo-pentofuranosyl)adenine (Compound A7b)

To a solution of the deoxy compound (Compound A6) (457 mg, 0.53 mmol) in anhydrous pyridine (3 ml) was added toluenesulfonyl chloride (1.00 g, 5.3 mmol), and the mixture was stirred at room temperature for 15 hours. The reaction mixture was cooled, treated with 50% aqueous pyridine, and extracted with chloroform. The organic layer was washed successively with water, aqueous sodium bicarbonate and water, and dried over magnesium sulfate. After distilling away the chloroform, the pyridine was removed as the toluene azeotrope, and the residue was subjected to silica gel column chromatography [eluant : toluene-ethyl acetate-triethylamine (95:5:1)]. The fractions containing the desired substance were combined and concentrated to give 241 mg of the tosylated compound (Compound A7b) (yield 45%)

PHYSICAL PROPERTIES OF COMPOUND A7b

Powders (Amorphous)

TCL Rf=0.70 (silica gel: chloroform-ethyl acetate methanol (8:2; 0.2)).

| IR spectrum (KBr) | | | |
|---|---|---|---|
| 3420 | 1367 | 1030 | 675 |
| 2940 | 1292 | 895 | 580 |
| 1600 | 1246 | 822 | 550 cm$^{-1}$ |
| 1503 | 1172 | | |

| $^1$H-NMR spectrum CDCl$_3$, δ | |
|---|---|
| 2.44 (1H, m, H-3') | 3.77 and 3.80 (12H, s, O—CH$_3$) |
| 2.56 (1H, m, H-3") | 4.24 (1H, m, H-4') |
| 2.15 (3H, s, C—CH$_3$) | 4.88 (1H, m, H-2') |
| 3.32 (1H, dd, H-5') | 6.03 (1H, d, H-1') |
| 3.41 (1H, dd, H-5") | 7.80 (1H, s, H-2) |
| | 7.95 (1H, s, H-8) |

EXAMPLE 5

Synthesis of
N$^6$,O$^{5'}$-bis(4,4'-dimethoxytrityl)-9-(2-(R)-azido-2,3-
dideoxy-β-D-glycero-pentofuranosyl)adenine
(Compound A8)

The 3'-deoxy-2'-O-mesylated compound (Compound A7) (523 mg, 0.56 mmol) was dissolved in N,N-dimethylformamide (12 ml), and sodium azide (1.09 g, 16.8 mmol) was added thereto, followed by stirring at 105°-110° C. for 5 hours. The reaction mixture was cooled and extracted with ether containing a small amount of chloroform. The extract was washed several times with water and dried over magnesium sulfate. The organic solvents were removed under reduced pressure, and the residue was subjected to silica gel column chromatography [eluant : chloroform-ethyl acetate-triethylamine (97:3:1)]to give 382 mg of the azide compound (Compound A8) (yield 78%).

PHYSICAL PROPERTIES OF COMPOUND A7

Powders (Amorphous)

| Elementary analysis | C | H | N |
|---|---|---|---|
| Calculated (%) (for C$_{52}$H$_{48}$N$_8$O$_6$.0.5H$_2$O) | 70.18 | 5.55 | 12.59 |
| Found (%) | 70.26 | 5.53 | 12.45 |

Specific rotations: $[\alpha]_D^{20} = -37.5°$ (c=0.4, CHCl$_3$).
UV spectrum $\lambda_{max}^{MeOH}$274 nm (ε28,900).

| IR spectrum (KBr) | | |
|---|---|---|
| 3420 | 1505 | 823 |
| 2950 | 1248 | 700 |
| 2100 (N$_3$) | 1173 | 580 cm$^{-1}$ |
| 1600 | 1030 | |

| $^1$H-NMR spectrum CDCl$_3$, δ | |
|---|---|
| 2.13 (1H, ddd, H-3') | 4.53 (1H, m, H-4') |
| 2.41 (1H, m, H-3") | 4.82 (1H, m, H-2') |

-continued

| | |
|---|---|
| 3.33 (1H, dd, H-5') | 5.98 (1H, d, H-1') |
| 3.41 (1H, dd, H-5") | 7.94 (1H, s, H-2) |
| 3.77 (12H, s, O—CH$_3$) | 8.03 (1H, s, H-8) |

EXAMPLE 6

Synthesis of 9-(2-azido-2,3-dideoxy-β-D-glyceropentofuranosyl)adenine (Compound A9)

A mixture of the DMTr-protected 2'-azide compound (Compound A8) (182 mg, 0.21 mmol) and 80% acetic acid (6.8 ml) was stirred at room temperature for 4 hours. Acetic acid was removed under reduced pressure by co-evaporation with toluene-ethanol, and a small amount of ethanol was added to the residue to deposit the free 2'-azide compound (Compound A9) as crystals (26 mg, yield 43%). The mother liquor where the crystals had been removed was concentrated, and the residue was subjected to silica gel column chromatography [eluant: chloroform-methanol (95:5)]. The fractions containing the desired product were combined and concentrated to give Compound A9 (19 mg, yield 32%; total 75%).

PHYSICAL PROPERTIES OF COMPOUND A9

Colorless Crystals

Melting point: 203°–204° C. (dec.).

| | Elementary analysis | | |
|---|---|---|---|
| | C | H | N |
| Calculated (%) | 43.47 | 4.38 | 40.56 |
| (for C$_{10}$H$_{12}$N$_8$O$_2$) | | | |
| Found (%) | 43.47 | 4.38 | 40.60 |

Specific rotations: $[\alpha]_D^{22} = -66.0°$ (c=0.6, DMF).
UV Spectrum $\lambda_{max}^{MeOH}$ 258 nm (ε15,000).

| IR Spectrum (KBr) | | |
|---|---|---|
| 3400 | 3140 | 2120 (N$_3$) |
| 1695 | 1610 | 1480 |
| 1422 | 1295 | 1174 |
| 1120 | 1096 | 1068 |
| 1010 | 952 | 795 |
| 721 | 632 | 543 cm$^{-1}$ |
| $^1$H-NMR Spectrum DMSO-d6, δ | | |
| 2.14 (1H, m, H-3') | 4.85 (1H, m, H-2') | |
| 2.46 (1H, m, H-3") | 5.25 (1H, t, OH) | |
| 3.54 (1H, m, H-5') | 6.01 (1H, d, H-1') | |
| 3.72 (1H, m, H-5") | 7.36 (2H, br s, NH$_2$) | |
| 4.32 (1H, m, H-4) | 8.16 (1H, s, H-2) | |
| | 8.40 (1H, s, H-8) | |

EXAMPLE 7

Synthesis of N$^6$,O$^5$=-bis(4,4'-dimethoxytrityl)-9-(2-(R)-iodi-2,3-dideoxy-β-D-glycero-pentofuranosyl)adenine (Compound A10)

To a solution of the 2'-tosylated compound (Compound A7b) (160 mg, 0.16 mmol) in N,N-dimethylformamide (1 ml) was added lithium iodide (212 mg, 1.60 mmol) and the mixture was stirred at 105°–110° C. for 5 hours. After cooling, the reaction mixture was diluted with ether containing a small amount of chloroform. The solution was washed several times with water and dried over magnesium sulfate. The drying agent was removed by filtration and the filtrate was concentrated under reduced pressure The resulting residue was subjected to silica gel chromatography [silica gel 10 g; eluant, toluene - ethyl acetate - triethylamine (30:1:0.3)]and preparative TLC [(silica gel 200×200×2 mm; developing solvent; benzene - ethyl acetate - methanol - triethylamine (9:1:0.15:0.1)] to afford 80 mg of the 2'-iodo compound (Compound A10) (yield 52%). An analytical sample was prepared by dropwise adding a dichloromethane solution of the iodo compound to pentane, followed by collecting the resulting precipitates by filtration and drying it.

PHYSICAL PROPERTIES OF COMPOUND A10

Powders (Amorphous)

| | Elementary analysis | | |
|---|---|---|---|
| | C | H | N |
| Calculated (%) | 65.07 | 5.27 | 7.09 |
| (for C$_{52}$H$_{48}$N$_5$O$_6$I.0.3C$_5$H$_{12}$) | | | |
| Found (%) | 64.95 | 5.18 | 6.81 |

| IR Spectrum (KBr) | | | | |
|---|---|---|---|---|
| 3445 | 1604 | 1465 | 1174 | 703 |
| 2955 | 1583 | 1294 | 1031 | 584 |
| 2870 | 1507 | 1250 | 826 | |
| $^1$H-NMR Spectrum CDCl$_3$ δ | | | | |
| 2.35 (1H, m, H-3') | | 4.99 (1H, dt, H-2') | | |
| 2.58 (1H, m, H-3") | | 6.42 (1H, d, H-1') | | |
| 3.39 (1H, dd, H-5') | | 6.77–6.86, 7.15–7.41 | | |
| 3.45 (1H, dd, H-5") | | (27H, m, arom, NH) | | |
| 3.77, 3.78 and 3.79 | | 7.90 (1H, s, H-2) | | |
| (12H, s, OMe) | | 8.03 (1H, s, H-8) | | |
| 4.66 (1H, m, H-4') | | | | |

EXAMPLE 8

Synthesis of N$^6$,O$^5'$-bis(4,4'-dimethoxytrityl)-9-(2,3-dideoxy-62-D-glycero-pentofuranosyl)adenime (Compound A11)

The 2'-iodo compound (Compound A10) (217 mg, 0.22 mmol) was dissolved in previously degassed toluene (5 ml). Tributyltin hydride (91 μl, 0.34 mmol) and α,α'-azobisisobutyronitrile (5 mg, 0.03 mmol) were added thereto under an atmosphere of nitrogen, and the mixture was stirred at 80° C. for 20 minutes. After cooling, the reaction mixture was concentrated under reduced pressure, and the residue was purified by silica gel chromatography silica gel 15 g; eluant, toluene - ethyl acetate - triethylamine (50:1:0.5)]to give 156 mg of the dideoxy compound (Compound A11) (yield 83%).

PHYSICAL PROPERTIES OF COMPOUND A11

Amorphous

| | Elementary analysis | | |
|---|---|---|---|
| | C | H | N |
| Calculated (%) | 73.02 | 5.97 | 8.19 |
| (for C$_{52}$H$_{49}$N$_5$O$_6$.0.85H$_2$O) | | | |
| Found (%) | 73.32 | 6.05 | 7.89 |

| IR Spectrum (KBr) cm$^{-1}$ | | | | |
|---|---|---|---|---|
| 3445 | 1605 | 1297 | 1073 | 705 |

-continued

| 2980 | 1507 | 1250 | 1032 | 585 |
|------|------|------|------|-----|
| 2860 | 1463 | 1170 | 826  |     |

$^1$H-NMR Spectrum (CDCl$_3$) δ

| | |
|---|---|
| 2.05 (2H, m, H-3') | 6.27 (1H, dd, H-1') |
| 2.49 (2H, m, H-2') | 6.76–6.72 |
| 3.32 (2H, d, H-5') | (8H, each, d, arom H) |
| 3.76 (12H, s, OMe) | 6.88 (1H, s, NH) |
| 4.33 (1H, m, H-4') | 7.18–7.43 (18H, m, arom) |
| | 7.94 (1H, s, H-2) |
| | 8.04 (1H, s, H-8) |

REFERENCE EXAMPLE 2

Synthesis of 9-(2,3-dideoxy-β-D-glycero-pentofuranosyl)adenine(-dideosyadenosine) (Compound A12)

The dimethoxytrityl-protected 2',3'-dideoxy compound (Compound A11) (65 mg, 0.077 mmol) was dissolved in chloroform (385 μl,) and a solution of zinc bromide (AnBr$_2$ 141 mg, 0.62 mmol) in methanol (182 μl) - chloroform (676 μl) was added thereto, followed by stirring at room temperature for about 4 hours. After completion of the reaction methanol (2 ml) was added and chloroform was distilled off under reduced pressure with such precaution that the reaction solution is not evaporated to dryness. Water was added to the resulting methanol solution, the resulting precipitate of trityl alcohol was removed by filtration and the filtrate was passed through a HP-20 column (10×130 mm) (eluant; water-30% methanol). The fractions containing the desired substance were concentrated under reduced pressure, and the residue was purified using Domex 1-X2 (OH- form, eluant; methanol) and recrystallized from ethanol to afford the desired dideoxyadenosine (Compound A12) as colorless crystals. Yield 8 mg (44%).

Compound A12 is the known compound, and its physical properties are disclosed in M. J. Robins, J. R. McCarthy, R. K. Robins, Biochem., 5, 224 (1966).

PHYSICAL PROPERTIES OF COMPOUND A12

Melting point: 185°–186° C.

| NMR Spectrum (D$_2$O) δ from DSS | |
|---|---|
| 2.04 (1H, m, H-3') | 4.36 (1H, m, H-4') |
| 2.23 (1H, m, H-3'') | 6.29 (1H, dd, H-1') |
| 2.52 (1H, m, H-2') | 8.18 (1H, s, H-2) |
| 2.57 (1H, m, H-2'') | 8.30 (1H, s, H-8) |
| 3.66 (1H, dd, H-5') | |
| 3.82 (1H, dd, H-5'') | |

EXAMPLE 9

Synthesis of N$^4$,O$^{2'}$,O$^{5'}$-tripivaloyl-3'-O-methanesulfonylcytosine (Compound C3)

Pivaloyl chloride (19.8 ml, 160 mmol) was added all at once to a solution of cytidine (972 g, 40 mmol) in pyridine (140 ml) under ice cooling, followed by stirring at room temperature for 90 minutes. Then, methanesulfonyl chloride (186 ml, 240 mmol) was added under ice cooling, followed by stirring at room temperature for one hour. After cooling, an aqueous 50% pyridine solution was added to decompose an excess of the reagent, and the mixture was extracted with ether. The organic layer was washed successively with aqueous sodium bicarbonate and aqueous saturated sodium chloride, and dried over magnesium sulfate. After evaporating the solvent under reduced pressure, the remaining pyridine was removed by co-evaporation with toluene, and the residue was subjected to silica gel column chromatography [eluant, benzene-ethyl acetate (2:1) ]to give 18.3 g of the desired 3'-mesylated compound (Compound C3) (yield 80%). An analytical sample was prepared by dropwise adding a dichloromethane solution of Compound C3 to n-pentane and drying the resulting precipitates.

PHYSICAL PROPERTIES OF COMPOUND C3

Amorphous

| Elementary analysis | | | | |
|---|---|---|---|---|
| | C | H | N | S |
| Calculated (%) (for C$_{25}$H$_{39}$N$_3$O$_{10}$I.0.2H$_2$O) | 52.02 | 6.88 | 7.28 | 5.55 |
| Found (%) | 51.93 | 6.80 | 7.21 | 5.55 |

| IR Spectrum (KBr) cm$^{-1}$ | | | | | |
|---|---|---|---|---|---|
| 3450 | 2705 | 1632 | 1315 | 1142 | 530 |
| 3380 | 1736 | 1557 | 1280 | 975 | |
| 3000 | 1720 | 1483 | 1180 | 928 | |
| 2960 | 1670 | 1370 | 1140 | 845 | |

$^1$H-NMR Spectrum (CDCl$_3$) δ

| | |
|---|---|
| 1.26 (9H, s, C(CH$_3$)$_3$) | 5.30 (1H, t, H-3') |
| 1.27 (9H, s, C(CH$_3$)$_3$) | 5.49 (1H, dd, H-2') |
| 1.29 (9H, s, C(CH$_3$)$_3$) | 6.01 (1H, d, H-1') |
| 3.07 (3H, s, SO$_2$CH$_3$) | 7.47 (1H, d, H-5) |
| 4.44 (2H, d, H-5', H-5'') | 7.82 (1H, d, H-6) |
| 4.52 (1H, m, H-4') | 8.19 (1H, br s, NH) |

REFERENCE EXAMPLE 3

Synthesis of 1-(3-deoxy-β-D-threo-pentofuranosyl) cytosine (Compound C4a, C4b and C4c)

Compound C3 (241 g, 4.20 mmol) was dissolved in a mixture of benzene (4 ml) and methanol (4 ml), and magnesium methoxide (1.19 g, 13.8 mmol) and sodium borohydride (321 mg, 8.49 mmol) were added at room temperature, followed by stirring for 10 hours. After cooling, aceton (2 ml) was added to decompose an excess of the reagent, an aqueous ammonium chloride solution was added, and the deposited precipitates were removed by filtration. The filtrate was partitioned between ethyl acetate and water, and the ethyl acetate layer was further washed twice with water. The thus obtained water layer was passed through a column packed with HP-20 (Dowex Co., styrene-divinylbenzene polymer, 50 ml) to adsorb by-products, and the desired C4a product was eluted with water (about 1 l). Then, an activated carbon (50 ml, Wako Junyaku Co., Ltd., for column choromatography) was added to this aqueous solution, followed by stirring for 20 minutes. The activated carbon was separated by filtration, and after washing with water the adsorbed organic substance was eluted with methanol to provide the desired 3'-deoxy threo compound (C4a) along with its erythro isomer (786 mg, yield 83%, threo : erythro 93:7). Since Compound C4a has a strong hygroscopic property and is hard to be purified, it was crystallized from methanol as the picrate (C4b) or as the hydrochloride (C4c).

PHYSICAL PROPERTIES OF COMPOUND C4a

Amorphous

| IR Spectrum (KBr) cm$^{-1}$ | | |
|---|---|---|
| 3380 | 1490 | 1123 |
| 2960 | 1395 | 1063 |
| 1647 | 1289 | 786 |
| 1605 | 1200 | 600 |

| $^1$H-NMR Spectrum (DMSO-d6) δ | |
|---|---|
| 1.74 (1H, ddd, H-3') | 5.67 (1H, d, H-5) |
| 2.27 (1H, ddd, H-3") | 5.88 (1H, d, H-1') |
| 3.55 (1H, m, H-5') | 7.68 (1H, d, H-6) |
| 3.99–4.04 (1H, m, H-4') | 6.9–7.1 (2H, brs, NH$_2$) |
| 4.24–4.29 (1H, m, H-2') | |
| 5.08 (1H, m, OH) | |
| 5.18 (1H, d, OH) | |

PHYSICAL PROPERTIES OF COMPOUND C4b

Melting point: 208°–209° C. (dec.).

| IR Spectrum (KBr) cm$^{-1}$ | | | | |
|---|---|---|---|---|
| 3600 | 1695 | 1550 | 1120 | 820 |
| 3350 | 1675 | 1335 | 1082 | 790 |
| 3130 | 1610 | 1315 | 1035 | 740 |
| 2980 | 1575 | 1265 | 910 | 710 |
| | | | | 623 |

| $^1$H-NMR Spectrum (DMSO-d6) δ | |
|---|---|
| 1.75 (1H, m, H-3') | 6.05 (1H, d, H-5) |
| 2.26 (1H, m, H-3") | 8.13 (1H, d, H-6) |
| 3.60 (2H, m, H-5', 5") | 8.59 (2H, s, arom) |
| 4.08 (1H, m, 4') | 9.45 (1H, br s, N$^+$—H) |
| 4.40 (1H, m, H-2') | |
| 5.19 (1H, d, H-1') | |

PHYSICAL PROPERTIES OF COMPOUND C4c

Melting point: 183.5°–184.5° (dec.).

| Elementary analysis | C | H | N | S |
|---|---|---|---|---|
| Calculated (%) (for C$_{19}$H$_{13}$N$_3$O$_4$.HCl) | 41.00 | 5.35 | 15.94 | 13.45 |
| Found (%) | 41.00 | 5.38 | 15.90 | 13.55 |

Specific rotations: $[\alpha]_D^{26}+151°$ (c=0.5, H$_2$O).

| IR Spectrum (KBr) cm$^{-1}$ | | | | |
|---|---|---|---|---|
| 3460 | 1700 | 1382 | 1072 | 780 |
| 3240 | 1675 | 1284 | 982 | 700 |
| 3040 | 1635 | 1118 | 930 | 609 |
| 2750 | 1540 | 1092 | 810 | 590 |

EXAMPLE 10

Synthesis of 2',5'-di-O-pivaloyl-3'-O-methanesulfonylcytidine (Compound C5)

Compound C3 (667 mg, 1.16 mmol) was dissolved in a mixture of benzene (1 ml) and methanol (1 ml), and magensium methoxide (150 mg, 1.74 mmol) was added to this solution, followed by stirring at room temperature for 30 minutes. The reaction mixture was cooled, an aqueous saturated ammonium chloride solution was added, and the mixture was extracted with ether containing a small amount of chloroform. The organic layer was washed twice with saturated aqueous sodium chloride and dried over magnesium sulfate. The solvents were evaporated under reduced pressure and the residue was subjected to silica gel column chromatography [eluant: chloroform-methanol (50:1)] to give Compound C5 (495 mg, yield 87%).

An analytical sample was prepared by dropwise adding a dichloromethane solution of Compound C5 to pentane and drying the resulting precipitates.

PHYSICAL PROPERTIES OF COMPOUND C5

Amorphous

| Elementary analysis | C | H | N | S |
|---|---|---|---|---|
| Calculated (%) (for C$_{20}$H$_{31}$N$_3$O$_9$S) | 49.07 | 6.38 | 8.58 | 6.55 |
| Found (%) | 48.95 | 6.34 | 8.49 | 6.50 |

Specific rotations: $[\alpha]_D^{20}+41.8°$ (c=0.3, CHCl$_3$).

| IR Spectrum (KBr) cm$^{-1}$ | | | |
|---|---|---|---|
| 3370 | 1650 | 1180 | 930 |
| 3000 | 1484 | 1145 | 790 |
| 2960 | 1369 | 1040 | 532 |
| 1736 | 1285 | 975 | |

| NMR Spectrum (CDCl$_3$) δ | |
|---|---|
| 1.24 (9H, s, C(CH$_3$)$_3$) | 5.72 (1H, d, H-1') |
| 1.26 (9H, s, C(CH$_3$)$_3$) | 5.87 (1H, d, H-5) |
| 3.08 (3H, s, SO$_2$CH$_3$) | 7.38 (1H, d, H-6) |
| 4.47–4.35 (3H, m, H-4', H-5', H-5") | |
| 5.40 (1H, t, H-3') | |
| 5.49 (1H, dd, H-2') | |

EXAMPLE 11

Synthesis of N$^4$-(4,4'-dimethoxytrityl)-2',5'-di-O-pivaloyl-3'-O-methanesulfonylcytidine (Compound C6)

4,4'-Dimethoxytrityl chloride (685 mg, 2.02 mmol) was added to a solution of Compound C5 (825 mg, 1.69 mmol) in anhydrous pyridine (4 ml) and the mixture was stirred at room temperature for 3 hours. After cooling, aqueous 50% pyridine was added to decompose an excess of the reagent, and the mixture was extracted with ether containing a small amount of chloroform. The organic layer was washed with aqueous sodium bicarbonate and dried over magnesium sulfate. The organic solvents were evaporated, the remaining pyridine was removed as the toluene azeotrope and the residue was subjected to silica gel chromatography [eluant; chloroform-ethyl acetate-triethylamine (80:20:1)]to give 1.280 g of the desired compound, C6 (yield 96%).

An analytical sample was prepared by dropwise adding a dichloromethane solution of Compound C6 to pentane and drying the resulting precipitates.

PHYSICAL PROPERTIES OF COMPOUND C6

Amorphous

| Elementary analysis | C | H | N | S |
|---|---|---|---|---|
| Calculated (%) (for C$_{41}$H$_{49}$N$_3$O$_{11}$S.0.5H$_2$O) | 61.49 | 6.29 | 5.25 | 4.00 |
| Found (%) | 61.61 | 6.21 | 5.25 | 3.97 |

Specific rotations: $[\alpha]_D^{20}+4.0°$ (c=0.5, CHCl$_3$).

| IR Spectrum (KBr) cm$^{-1}$ | | | | |
|---|---|---|---|---|
| 3430 | 1662 | 1497 | 1180 | 779 |
| 2990 | 1653 | 1365 | 1144 | 702 |
| 2950 | 1635 | 1280 | 1032 | 587 |
| 1735 | 1506 | 1256 | 829 | 525 |

| $^1$H-NMR Spectrum (CDCl$_3$) δ | |
|---|---|
| 1.14 (9H, s, C(CH$_3$)$_3$) | 5.32 (1H, br t, H-3') |
| 1.26 (9H, s, C(CH$_3$)$_3$) | 5.53 (1H, dd, H-2') |
| 3.05 (3H, s, S–CH$_3$) | 5.73 (1H, d, H-1') |
| 3.80 (3H, s, O–CH$_3$) | 6.82 (5H, br d) |
| 4.32–4.42 (3H, m) | 7.08–7.33 (10H, m) |
| 5.05 (1H, d, H-5) | |

EXAMPLE 12

Synthesis of
N$^4$-(4,4'-dimethoxytrityl)-1-(3-deoxy-β-D-threo-pentofuranosyl)cytosine (Compound C7)

Compound C6 (50 mg, 0.063 mmol) was dissolved in a mixture of benzene (0.5 ml) and methanol (0.5 ml), and magnesium methoxide (27 mg, 0.313 mmol) and sodium borohydride (12 mg, 0.317 mmol) were added, followed by stirring for 10 hours. After cooling acetone (0.1 ml) was added to decompose an excess of the reagents, and the mixture was extracted with ether containing a small amount of chloroform. The organic layer was washed with aqueous sodium bicarbonate and dried over magnesium sulfate. The organic solvents were evaporated, the remaining pyridine was removed as the toluene azeotrope, and the residue was subjected to silica gel column chromatography (eluant; chloroform-methanol-triethylamine (100:2:1)) to afford the desired 3'-deoxy threo compound C7 and its epimer, erythro compound (total 30 mg) (yield 90%, threo : erythro =93:7).

The compound is C7 difficult for separation from its epimer, and was used, without purification, for further reaction.

EXAMPLE 13

Synthesis of
N$^4$-(4,4'-dimethoxytrityl)-1-(3-deoxy-β-D-threo-pentofuranosyl)cytosine (Compound C7)

Reaction was carried out in a manner similar to that in Example 12 using Compound C6 (236 mg, 0.298 mmol) and magnesium methoxide (129 mg, 1.494 mmol). Tetra-n-butylammonium borohydride (383 mg, 1.488 mmol) was used in place of sodium borohydride. As the result, 142 mg of the desired 3'-deoxy threo compound C7 and an erthro isomer were obtained (yield 90%, threo compound : erythro =93:7).

PHYSICAL PROPERTIES OF COMPOUND C7

Amorphous

| IR Spectrum (KBr) cm$^{-1}$ | | |
|---|---|---|
| 3400 | 1250 | 830 |
| 2950 | 1180 | 782 |
| 1635 | 1115 | 702 |
| 1505 | 1030 | 585 |

| NMR Spectrum (CDCl$_3$) δ | |
|---|---|
| 2.02 (1H, m, H-3') | 4.28 (1H, m, H-4') |
| 2.39 (1H, m, H-3'') | 4.57 (1H, m, H-2') |
| 3.63 (1H, dd, H-5') | 5.07 (1H, d, H-5) |
| 3.79 and 3.80 (6H, each, s, OCH$_3$) | 5.90 (1H, d, H-1') |
| 3.88 (1H, dd, H-5'') | 6.80–6.85, 7.12–7.30 (m, arom) |
| | 7.57 (1H, d, H-6) |

EXAMPLE 14

Synthesis of
N$^4$,O$^{5'}$-bis(4,4'-dimethoxytrityl)-1-(3-deoxy-β-D-threo-pentofuranosyl)cytosine (Compound C8a)

The mono DMTr compound (Compound C7, 530 mg, 1.0 mmol) was dissolved in anhydrous pyridine (5 ml), and 4,4'-dimethoxytrityl chloride (407 mg, 1.2 mmol) was added thereto, followed by stirring at room temperature for 2 hours. After cooling, 50% aqueous pyridine was added to decompose an excess of the reagent, and the mixture was extracted with ether. The organic layer was washed successively with aqueous sodium bicarbonate and water, dried over anhydrous magnesium sulfate, and concentrated under reduced pressure. The pyridine was removed as the toluene azeotrope. The residue was subjected to silica gel chromatography [eluant; benzene-ethyl acetate-triethylamine-methanol (50:50:1:1)], and the fractions containing the desired substance were combined and concentrated to give 594 mg of the di-DMTr compound (Compound C8a) (yield 71%).

PHYSICAL PROPERTIES OF COMPOUND C8a

Amorphous

| | Elementary analysis | | |
|---|---|---|---|
| | C | H | N |
| Calculated (%) (for C$_{51}$H$_{51}$N$_3$O$_8$) | 73.45 | 6.16 | 5.04 |
| Found (%) | 73.20 | 6.46 | 4.79 |

Specific rotations: [α]$_D^{25}$= +17.1° (c=1.1, CHCl$_3$).
TLC Rf=0.53 (Silica gel: CHCl$_3$—MeOH (9:1)).
UV spectrum λ$_{max}^{MeOH}$281 nm (ε17,400).

| IR spectrum (KBr) cm$^{-1}$ | | | |
|---|---|---|---|
| 3420 | 1643 | 1180 | 702 |
| 2960 | 1510 | 1034 | 584 |
| 2850 | 1252 | 830 | |

| $^1$H-NMR Spectrum (CDCl$_3$) δ | |
|---|---|
| 2.04 (1H, m, H-3') | 4.15 (1H, m, H-4') |
| 2.20 (1H, m, H-3'') | 4.68 (1H, m, H-2') |
| 3.28 (1H, dd, H-5') | 4.82 (1H, d, H-5) |
| 3.41 (1H, dd, H-5'') | 5.98 (1H, d, H-1') |
| 3.73, 3.74 and 3.75 (12H, each s, O–CH$_3$) | 6.72–7.34 (m, arom) |
| | 7.90 (1H, d, H-6) |

EXAMPLE 15

Synthesis of
N$^4$,O$^{5'}$-dipivaloyl-1-(3-deoxy-β-D-threo-pentofuranosyl)cytosine (Compound C8b)

The diol compound (Compound C4a, 180 mg, 0.799 mmol), prepared according to the method (Example 10), was dissolved in anhydrous pyridine (2 ml), and pivaloyl chloride (230 μl, 1.87 mmol) was added thereto, followed by stirring at room temperature for 6 hours. After cooling, water was added to decompose an excess of the reagent, and the mixture was extracted with ether containing a small amount of chloroform. The organic layer was washed successively with aqueous sodium bicarbonate and aqueous saturated sodium chloride, dried over anhydrous magnesium sulfate, and concentrated under reduced pressure. The pyridine was removed as the toluene azeotrope and the residue was subjected to silica gel column chromatography [eluant; chloroform-methanol (50:1)]to provide 250 mg of the desired dipivaloylated compound (Compound C8b) (yield 79%) and its erythro isomer (25 mg, yield 8%).

PHYSICAL PROPERTIES OF COMPOUND C8b

Colorless Crystals

Melting point: 150°–151° C.

| Elementary analysis | | | |
|---|---|---|---|
| | C | H | N |
| Calculated (%) (for $C_{19}H_{29}O_6N_3 \cdot HCl$) | 57.71 | 7.39 | 10.63 |
| Found (%) | 57.64 | 7.34 | 10.58 |

Specific rotations: $[\alpha]_D^{24} = +134°$ (c=0.5, $CHCl_3$).

| IR Spectrum (KBr)cm$^{-1}$ | | | | |
|---|---|---|---|---|
| 3450 | 1648 | 1395 | 1128 | 920 |
| 3000 | 1618 | 1310 | 1100 | 803 |
| 2900 | 1558 | 1278 | 1035 | 625 |
| 1716 | 1485 | 1157 | 1015 | |

| $^1$H—NMR Spectrum ($CDCl_3$) | |
|---|---|
| 1.26 (9H, s, $C(CH_3)_3$) | 4.52 (1H, dd, H-5") |
| 1.29 (9H, s, $C(CH_3)_3$) | 4.88 (1H, ddd, H-2') |
| 1.8–2.1 (1H, br s, OH) | 5.97 (1H, d, H-1') |
| 1.95 (1H, ddd, H-3') | 7.46 (1H, d, H-5) |
| 2.43 (1H, ddd, H-3") | 8.10 (1H, d, H-6) |
| 4.21 (1H, dd, H-5') | 8.20 (1H, br s, NH) |
| 4.42–4.45 (1H, m, H-4') | |

EXAMPLE 16

Synthesis of $N^4,O^{5'}$-bis(4,4'-dimethoxytrityl)-1-(3-deoxy-2-O-mesyl-β-D-threo-pentofuranosyl)cytosine (Compound C9a)

Methanesulfonyl chloride (0.132 ml, 1.7 mmol) was added to a solution of Compound C8a (470 mg, 0.56 mmol) in anhydrous pyridine (3 ml) and the mixture was stirred for 4.5 hours. After cooling, ice water was added to decompose an excess of the reagent, and the mixture was extracted with ether containing a small amount of chloroform. The organic layer was washed successively with water, aqueous sodium bicarbonate and water, and dried over magnesium sulfate. The organic solvents were evaporated, the remaining pyridine was removed as the toluene azeotrope, and the residue was subjected to silica gel column chromatography [eluant; benzene-ethyl acetate-triethylamine-methanol (50:50:1:3)] to give 406 mg (yield 79%) of the mesylated compound (Compound C9a). An analytical sample was prepared by dropwise adding a dichloromethane solution of this mesylated compound to pentane and drying the resulting precipitates.

PHYSICAL PROPERTIES OF COMPOUND C9a

Amorphous

| Elementary analysis | | | | |
|---|---|---|---|---|
| | C | H | N | S |
| Calculated (%) | 69.56 | 6.66 | 4.27 | 3.26 |
| (for $C_{52}H_{53}N_3O_{10}S \cdot C_5H_{12}$) | | | | |
| Found (%) | 69.43 | 6.69 | 4.14 | 3.27 |

Specific rotations: $[\alpha]_D^{25} = +27.6°$ (c=1.0, $CHCl_3$).
TLC Rf=0.58 (Silica gel; $CHCl_3$-MeOH (9:1).
UV spectrum $\lambda_{max}^{MeOH}$ 276 nm (κ19,400).

| IR spectrum (KBr)cm$^{-1}$ | | | | |
|---|---|---|---|---|
| 3450 | 1660 | 1177 | 827 | 530 |
| 2970 | 1510 | 1032 | 705 | |
| 2860 | 1250 | 906 | 587 | |

| $^1$H—NMR Spectrum ($CDCl_3$) δ | |
|---|---|
| 2.28 (1H, ddd, H-3') | 4.17 (1H, m, H-4') |
| 2.49 (1H, ddd, H-3") | 5.31 (1H, q, H-2') |
| 2.88 (3H, s, C—$CH_3$) | 4.96 (1H, d, H-5) |
| 3.30 (2H, br s, H-5', 5") | 6.11 (1H, d, H-1') |
| 3.74, 3.75, 3.76 (m, arom.) and 6.75–7.36 | 7.56 (1H, d, H-6). |
| 3.77 (12H, each s, O—$CH_3$) | |

EXAMPLE 17

Synthesis of $N^4,O^{5'}$-bis(4,4'-dimethoxytrityl)-1-(3-deoxy-2-O-tosyl-β-D-threo-pentofuranosyl)cytosine (Compound C9b)

Compound C8a (250 mg, 0.30 mmol) was dissolved in anhydrous tetrahydrofuran (2 ml), and a t-butylmagnesium chloride-THF solution (1.7 M, 360 1, 0.61 mmol) and then p-toluenesulfonyl chloride (172 mg, 0.90 mmol) were added, followed by stirring at room temperature for 22 hours. The reaction mixture was poured in aqueous 2% sodium bicarbonate, and extracted with toluene. The extract was washed successively with aqueous saturated sodium bicarbonate and water, and dried over magnesium sulfate. Magnesium sulfate was removed by filtration, the filtrate was concentrated under reduced pressure, and the residue was purified by silica gel chromatography [10 g, eluant; chloroform-methanol-triethylamine (50:1:0.5)]to give 290 mg (yield 97%) of the 2'-tosylated compound (Compound C9b) as colorless glasses.

PHYSICAL PROPERTIES OF COMPOUND C9b

Amorphous

| IR Spectrum (KBr)cm$^{-1}$ | | | |
|---|---|---|---|
| 3430 | 1652 | 1172 | 825 |
| 2960 | 1505 | 1030 | 699 |
| 2860 | 1245 | 895 | 580 |

| $^1$H—NMR Spectrum ($CDCl_3$) δ | |
|---|---|
| 2.17 (1H, m, H-3') | 4.92 (1H, m, H-2') |
| 2.41 (1H, m, H-3") | 5.00 (1H, d, H-5) |
| 2.44 (3H, s, Ts) | 6.00 (1H, d, H-1') |
| 3.25 (2H, m, H-5) | 6.76–7.38 (31H, m, arom, NH) |
| 3.77, 3.75, 3.74 (12H, each s, OMe) | 7.55 (1H, d, H-6) |
| 4.14 (1H, m, H-4') | |

EXAMPLE 18

Synthesis of N$^4$,O$^{5'}$-dipivaloyl-1-(3-deoxy-2-0-tosyl-$\beta$-D-threo-pentofuranosyl)cytosine (Compound C9c)

Compound C8b (1.684 g, 4.28 mmol) was dissolved in dry tetrahydrofuran (15 ml), and sodium hydride (purity 60%, 257 mg, 6.92 mmol) was added under ice cooling, followed by stirring for 15 minutes. Further, p-toluenesulfonyl chloride (1.63 g, 8.39 mmol) was added and the mixture was stirred at room temperature for 3 hours. Ice water was added to quench the reaction and the mixture was extracted with ether containing a small amount of chloroform. The organic layer was washed successively with aqueous sodium bicarbonate and aqueous saturated sodium chloride, and dried over magnesium sulfate. The organic solvents were evaporated and the residue was subjected to silica gel column chromatography [eluant; chloroform-methanol (100:1)] to afford 1.73 g (yield 74%) of the desired tosylated compound C9c.

PHYSICAL PROPERTIES OF COMPOUND C9c

Colorless Crystals

Melting point: 175°-176° C.

| Elementary analysis | | | | |
|---|---|---|---|---|
| | C | H | N | S |
| Calculated (for C$_{26}$H$_{35}$N$_3$O$_8$S) | 56.82 | 6.42 | 7.65 | 5.83 |
| Found (%) | 56.78 | 6.48 | 7.55 | 5.70 |

Specific rotations: $[\alpha]_D^{24}$ +109° (c=0.6, CHCl$_3$).

| IR Spectrum (KBr)cm$^{-1}$ | | | | |
|---|---|---|---|---|
| 3450 | 1733 | 1626 | 1312 | 902 |
| 3000 | 1718 | 1558 | 1180 | 814 |
| 2950 | 1673 | 1486 | 1026 | 663 |

| $^1$H—NMR Spectrum (CDCl$_3$) $\delta$ | |
|---|---|
| 1.23 (9H, s, C(CH$_3$)$_3$) | 5.24 (1H, ddd, H-2') |
| 1.31 (9H, s, C(CH$_3$)$_3$) | 5.99 (1H, d, H-1') |
| 2.26 (1H, ddd, H-3') | 7.25–7.6 (4H, m, arom) |
| 2.42 (3H, s, ArMe) | 7.60 (1H, d, H-5) |
| 2.58 (1H, ddd, H-3'') | 7.87 (1H, d, H-6) |
| 4.22 (1H, dd, H-5') | |
| 4.35–4.43 (2H, m, H-5'', H-4') | |

EXAMPLE 19

Synthesis of N$^4$,O$^{5'}$-dipivaloyl-1-(3-deoxy-2-O-phenoxythiocarbonyl-$\beta$-D-threo-pentofuranosyl)cytosine (Compound C9d)

Compound C8b (100 mg, 0.25 mmol) was dissolved in acetonitrile (2 ml), and N,N-dimethylaminopyridine (80 mg, 0.66 mmol) and phenyl chlorothionocarbonate (40 1, 0.33 mmol) were added, followed by stirring at room temperature for 20 hours. Water was added to the reaction mixture and extracted with chloroform, and the organic layer was washed successively with water, aqueous saturated sodium bicarbonate and water, and dried over magnesium sulfate. The drying agent was removed by filtration, the filtrate was concentrated under reduced pressure, and the residue was purified by preparative TLC [200×200×2 mm, developing solvent; chloroform-methanol (9:1)] to give 73 mg of Compound C9d as colorless glasses (yield 53%).

PHYSICAL PROPERTIES OF COMPOUND C9d

Amorphous

| IR Spectrum (film) cm$^{-1}$ | | |
|---|---|---|
| 3420 | 1638 | 1270 |
| 3000 | 1557 | 1205 |
| 1732 | 1488 | 1125 |
| 1715 | 1398 | 799 |
| 1671 | 1310 | 735 |

| $^1$H—NMR Spectrum (CDCl$_3$) $\delta$ | |
|---|---|
| 1.26 (9H, s, piv) | 6.03 (1H, m, H-2') |
| 1.30 (9H, s, piv) | 6.28 (1H, d, H-1') |
| 2.29 (1H, m, H-3') | 6.98 (1H, d, H-5) |
| 2.75 (1H, m, H-3'') | 7.24–7.48 (5H, m, Ph) |
| 4.35 (2H, m, H-5') | 7.98 (1H, d, H-6) |
| 4.48 (1H, m, H-4') | 8.13 (1H, br s, amide) |

EXAMPLE 20

Synthesis of N$^4$,O$^{5'}$-dipivaloyl-1-(3-deoxy-2-O-imidazoylthiocarbonyl-$\beta$-D-threo-pentofuranosyl)cytosine (Compound C9e)

Compound C8b (80 mg, 0.20 mmol) and 1,1'-thiocarbonyldiimidazole (50 mg, 0.28 mmol) were dissolved in acetonitrile (1 ml) and the solution was stirred at room temperature for 20 hours. The organic solvent was evaporated and the residue was subjected to silica gel column chromatography [eluant; chloroform-methanol (50:1) ]to afford 83 mg of the desired compound C9e (yield 81%).

PHYSICAL PROPERTIES OF COMPOUND C9e

Amorphous

| $^1$H—NMR Spectrum (CDCl$_3$) | |
|---|---|
| 1.21 (9H, s, C(CH$_3$)$_3$) | 6.20 (1H, d, H-1') |
| 1.28 (9H, s, C(CH$_3$)$_3$) | 6.25 (1H, m, H-2') |
| 2.19 (1H, ddd, H-3') | 7.01, 7.41 (2H, each, m, arom.) |
| 2.83 (1H, ddd, H-3'') | 7.55 (1H, d, H-5) |
| 4.14 (1H, dd, H-5') | 8.10 (1H, brs, NH) |
| 4.47–4.53 (2H, m, H-4', H-5'') | 8.12 (1H, d, H-6) |
| | 8.12 (1H, s, arom.) |

EXAMPLE 21

Synthesis of N$^4$,O$^{5'}$-bis(4,4'-dimethoxytrityl)-1-[(2R)-2-azido-2,3-dideoxy-$\beta$-D-glycero-pentofuranosyl]cytosine (Compound C10)

The 3'-deoxy-2'-O -mesyl compound (Compound C9a) (287 mg, 0.32 mmol) was dissolved in N,N-dimethylformamide (4 ml), and sodium azide (102 mg, 1.58 mmol) was added thereto, followed by stirring at 115°–120° C. for 4 hours. The reaction mixture was cooled and extracted with ether, and the extract was washed several times with water and dried over magnesium sulfate. The ether was removed and the residue was subjected to silica gel chromatography [eluant; benzene-ethyl acetate-triethylamine-methanol (50:50:1:0.2)]to give 251 mg of the azide compound (Compound C10) (yield 93%).

PHYSICAL PROPERTIES OF COMPOUND C10

Amorphous

| Elementary analysis | | | |
|---|---|---|---|
| | C | H | N |
| Calculated (%) (for $C_{51}H_{50}N_6O_7$) | 71.31 | 5.87 | 9.79 |
| Found (%) | 71.11 | 5.86 | 9.52 |

Specific rotations: $[\alpha]_D^{25} = -31.0°$ (c=0.9, $CHCl_3$).
TLC Rf=0.66 Silica gel [benzene-ethyl acetate-methanol (1:1:0.1)].
UV spectrum $\lambda_{max}^{MeOH}$ 281 nm ($\epsilon$19,900).

| IR spectrum (KBr) $cm^{-1}$ | | | | |
|---|---|---|---|---|
| 3430 | 2110 ($N_3$) | 1248 | 1033 | 585 |
| 2980 | 1655 | 1175 | 825 | |
| 2850 | 1505 | 1102 | 702 | |
| $^1$H-NMR Spectrum ($CDCl_3$) $\delta$ | | | | |
| 1.77 (1H, dd, H-3') | | 4.27 (1H, d, H-2') | | |
| 2.04 (1H, m, H-3'') | | 4.72 (1H, d, H-5) | | |
| 3.30 (1H, dd, H-5') | | 5.89 (1H, br s, H-1') | | |
| 3.54 (1H, dd, H-5'') | | 6.7–7.3 (m, arom.) | | |
| 3.73 and 3.74 | | 7.84 (1H, d, H-6) | | |
| (12H, each s, $CH_3$) | | | | |
| 4.35 (1H, m, H-4') | | | | |

REFERENCE EXAMPLE 4

Synthesis of 1-[(2R)-2-azido-2,3-dideoxy-$\beta$-D-glycero-pentofuranosyl]cytosine (Compound C11)

A mixture of the DMTr-protected 2'-azido compound (Compound C10) (171 mg, 0.20 mmol) and 80% acetic acid (3 ml) was stirred at 50°–55° C. for 75 minutes. The acetic acid was removed under reduced pressure and azeotropy using toluene-ethanol, and a small amount of dichloromethane was added to the residue to deposit the free 2'-azide compound (Compound C11) as crystals (42 mg, yield 84%). An analytical sample was obtained by recrystallization from isopropyl alcohol.

PHYSICAL PROPERTIES OF COMPOUND C11

Melting point: 171°–172° C. (dec.).

| Elementary analysis | | | |
|---|---|---|---|
| | C | H | N |
| Calculated (%) (for $C_9H_{12}N_6O_3 \cdot 0.1H_2O$) | 42.55 | 4.84 | 33.08 |
| Found (%) | 42.48 | 4.75 | 33.02 |

Specific rotations: $[\alpha]_D^{25} = -42.6°$ (c=0.3, DMF).
UV spectrum $\lambda_{max}^{MeOH}$ 271 nm ($\epsilon$8,900).

| IR spectrum (KBr) $cm^{-1}$ | | | | |
|---|---|---|---|---|
| 3480 | 2130 ($N_3$) | 1620 | 1105 | 705 |
| 3300 | 1680 | 1500 | 970 | 595 |
| 3100 | 1656 | 1290 | 853 | |
| 2970 | 1639 | 1250 | 780 | |
| $^1$H-NMR Spectrum (DMSO-$d_6$) $\delta$ | | | | |
| 1.81 (1H, ddd, H-3') | | 5.14 (1H, t, OH) | | |
| 2.00 (1H, ddd, H-3'') | | 5.70 (1H, d, H-5) | | |
| 3.56 (1H, ddd, H-5') | | 5.72 (1H, d, H-1') | | |
| 3.78 (1H, ddd, H-5'') | | 7.14 (2H, br d, $NH_2$) | | |
| 4.20 (1H, m, H-4') | | 7.96 (1H, d, H-6) | | |
| 4.32 (1H, br d, H2') | | | | |

REFERENCE EXAMPLE 5

Synthesis of 1-(2,3-dideoxy-$\beta$-D-glycero-pent-2'-enofuranosyl)cytosine (Compound C12)

Method 1

A 25 weight % sodium methoxide-methanol solution (175 l) was added to a solution of the tosylated compound C9c (84 mg, 0.153 mmol) in methanol (2 ml), and the mixture was stirred under reflux for 24 hours. After cooling, aqueous saturated ammonium chloride was added to quench the reaction, and the by-products were extracted with ethyl acetate and removed. An activated carbon (manufactured by WAKO JUNYAKU Co., Ltd., for chromatography, 10 ml) was added to the resulting water layer to adsorb the organic matters. The resulting activated carbon was washed with water Elution with methanol gave 2.5 mg of the unsaturated compound C12 (yield 7.8%).

Method 2

The tosylated compound C9c (53 mg, 0.097 mmol) and potassium tert-butoxide (54 mg, 0.48 mmol) were dissolved in tert-butyl alcohol (1 ml), and the solution was stirred at 60° C. for 30 minutes. The reaction mixture was poured in aqueous saturated ammonium chloride and extracted with ethyl acetate. The organic layer was washed with aqueous saturated sodium chloride, dried over magnesium sulfate, and concentrated under reduced pressure. Saturated aqueous ammonia-methanol (1 ml) was added to the residue and the mixture was stirred at room temperature for 24 hours. The methanol was evaporated under reduced pressure and the residue was purified by silica gel column chromatography to give 16 mg of the desired unsaturated compound C12 (yield 79%).

Method 3

The same procedure as described in Method 2 was carried out except that sodium hydride (oil, purity 60%, 19 mg, 0.48 mmol) was used in place of potassium tert-butoxide. As the result, 10 mg of the desired unsaturated compound was obtained (yield 49%).

PHYSICAL PROPERTIES OF COMPOUND C12

| $^1$H-NMR Spectrum (DMSO-$d_6$) $\delta$ | |
|---|---|
| 3.57 (2H, m, H-5', H-5'') | 6.89 (1H, m, H-1') |
| 4.76 (1H, m, H-4') | 7.14 (2H, br d, $NH_2$) |
| 4.95 (1H, t, OH) | 7.68 (1H, d, H-6) |
| 5.70 (1H, d, H-5) | |
| 5.87 (1H, m, H-3') | |
| 6.33 (1H, m, H-2') | |

REFERENCE EXAMPLE 6

Synthesis of 1-(2,3-dideoxy-$\beta$-D-glycero-pentofuranosyl)cytosine (dideoxycytidine) (Compound C13)

The reduction was carried out according to the method of Horwitz et al. (J. P. Horwitz, J. Chua, M. Noel, and J. T. Donatti, J. Org. Chem., 32, 817 (1967)). The unsaturated compound C12 (50 mg, 0.239 m mol)

and 5% palladium-carbon (10 mg) in methanol (3 ml) was stirred under a hydrogen atmosphere for one hour. After removal of the insoluble materials by filtration, the solvent was evaporated under reduced pressure and the resulting residue was purified by silica gel column chromatography [eluant; chloroform-methanol (8:2)] to obtain 36 mg of the desired dideoxycytidine C13 (yield 71%).

PHYSICAL PROPERTIES OF COMPOUND C13

| $^1$H-NMR Spectrum (DMSO-$d_6$) | |
|---|---|
| 1.72-1.89 (3H, m, H-2', H-3', H-3'') | 7.10 (2H, br d, NH$_2$) |
| 2.21-2.30 (1H, m, H-2'') | 7.92 (1H, d, H-6) |
| 3.54 (1H, m, H-5') | |
| 3.68 (1H, m, H-5'') | |
| 4.01 (1H, m, H-4') | |
| 5.05 (1H, t, OH) | |
| 5.72 (1H, d, H-5) | |
| 5.93 (1H, dd, H-1') | |

EXAMPLE 22

Synthesis of 1-(3-deoxy-β-D-threo-pentofuranosyl)uracil (Compound U3)

Pivaloyl chloride (9.08 g, 75 mmol) was added to a solution of uridine (7.32 g, 30 mmol) in dry pyridine (100 ml) at 5° C., and the mixture was then stirred at room temperature for 30 minutes. After the reaction mixture had been cooled to 5° C., mesyl chloride (13.8 g, 120 mmol) was added thereto and stirred at room temperature for one hour. The reaction mixture was cooled again and the reaction was quenched with 50% aqueous pyridine. The product was extracted with ether containing a small amount of chloroform. The extract was washed with water, aqueous sodium bicarbonate, and then water, and dried over magnesium sulfate. The organic solvent was removed. The pyridine was removed by toluene azeotropic evaporation. The residue was dissolved in methanol (100 ml) and cooled to 5° C. A solution of potassium hydroxide (6.72 g, 120 mmol) in methanol (80 ml) was added thereto with stirring, and then immediately sodium borohydride (2.28 g, 60 mmol) was added thereto.

After the reaction mixture had been stirred at room temperature for 24 hours, the insoluble crystals were collected by filtration with through a Celite pad and washed with methanol.

The filtrate and the washings were combined and cooled to 5° C. A mixture of concentrated hydrochloric acid (9.8 ml, ca. 118 mmol) and methanol (37 ml) was added thereto. The precipitate was collected by filtration through a Celite pad and washed with methanol. The filtrate and washings were combined, concentrated to 40 ml, and cooled. Then a mixture of concentrated hydrochloric acid (2.1 ml) and methanol (10 ml) was added again and the insoluble materials were collected by filtration and washed with methanol. The filtrate and washings were concentrated and the water was removed three times by ethanol azeotropic co-evaporation. The residue was subjected to silica gel column chromatography [eluant: chloroform-methanol (99:1)] and the objective compound (Compound U3) (3.82 g, 56%) was eluted with the same solvent system (97:3→9:1).

An analytical sample was obtained by recrystallization from isopropyl alcohol.

PHYSICAL PROPERTIES OF COMPOUND U3

Melting point: 146°-147° C.

| | Elementary analysis | | |
|---|---|---|---|
| | C | H | N |
| Calculated (%) (for C$_9$H$_{12}$N$_2$O$_5$) | 47.37 | 5.30 | 12.28 |
| Found (%) | 47.18 | 5.26 | 12.38 |

Specific rotations: $[\alpha]_D^{20} = +97.7°$ (c=1.14, DMF).
UV Spectrum $\lambda_{max}^{MeOH}$ 263 nm (e 10,300).
IR Spectrum (KBr) cm$^{-1}$: 3430, 3270, 2960, 1620, 1452, 1436, 1407, 1278, 1197, 1122, 1065, 1032, 992, 921, 877, 810, 753, 718, 695, 633, 572, 540.

| $^1$H-NMR Spectrum (DMSO-$d_6$) δ | |
|---|---|
| 11.78 (1H, br s, H-3) | 4.33 (1H, m, H-2') |
| 7.74 (1H, d, H-6) | 4.00 (1H, m, H-4') |
| 5.87 (1H, d, H-1') | 3.60 (1H, dd, H-5') |
| 5.55 (1H, dd, H-5) | 3.55 (1H, dd, H-5'') |
| 5.35 (1H, br s, OH-2) | 2.24 (1H, m, H-3') |
| 5.05 (1H, br s, OH-5') | 1.75 (1H, m, H-3'') |

EXAMPLE 23

Synthesis of 9-(3-deoxy-β-D-threo-pentofuranosyl) guanine (Compound G3)

Guanosine (5.0 g, 17.7 mmol) was suspended in dry pyridine (50 ml). To the suspension was added pivaloyl chloride (9.8 ml) 79.6 mmol) under ice cooling, and the mixture was then stirred at room temperature for 45 minutes. After ice cooling, methanesulfonyl chloride (4.1 ml, 53.0 mmol) was added dropwise to the reaction mixture, after which it was first stirred at 0° C. for 1 hour and then at room temperature for 3 hours. The reaction mixture was cooled with iced water and a small amount of water was added thereto and the mixture was stirred for 30 minutes. The reaction mixture was extracted with chloroform-ether and the organic layer was washed with saturated aqueous sodium bicarbonate and then with water, and dried over magnesium sulfate. The drying agent was removed by filtration and the filtrate was evaporated. The residue was dissolved in toluene and the solvent was evaporated under reduced pressure. This procedure was repeated several times to completely remove the remaining pyridine.. The residue was dissolved in methanol (120 ml). Sodium methoxide (7.6 g, 140.7 mmol) and sodium borohydride (2.7 g, 71.4 mmol) were added to the solution, after which it was first stirred at room temperature for 1 hour and then at 50° C. for 5 hours. After ice cooling, a small amount of acetone was added to decompose an excess of NaBH4. Methanol (100 ml) was added to the mixture, after which it was concentrated to ½ volume. This procedure was repeated to remove methyl borate thus produced as a by-product. The reaction mixture was again cooled with ice, and concentrated hydrochloric acid was gradually added to neutralize. Then, water was added and the mixture was concentrated under reduced pressure. The residue from which alcohol had been removed completely was suspended in water (about 150 ml), and applied to HP-20 (DIAION: 600 ml made up with water, Mitsubishi Chemical Industries Ltd.) column. Water (about 1.5 l) was passed through the column to elute inorganic salts, and the product was then eluted with 5% methanol-water followed with 5% methanol - 0.1 M ammonia water. Fractions containing compound G3 were concentrated to dryness under reduced pressure and the residue was recrystallized from methanol to give colorless crystals (1.31 g, 27.8%). The mother liquor was dried up under reduced pressure, again subjected to HP-20 column chromatography (300 ml) and followed by the same procedures mentioned above to give compound G3 (0.55 g, 11.6%).

Total amount of the obtained products was 1.86 g (39%).

PHYSICAL PROPERTIES OF COMPOUND G3

Melting point >265° C. (235° C. sintered).

| Elementary analysis | | | |
|---|---|---|---|
| | C | H | N |
| Calculated (%) (for $C_9H_{12}N_2O_5$) | 44.05 | 5.03 | 25.69 |
| Found (%) | 43.86 | 4.85 | 25.49 |

Specific rotations: $[\alpha]_D^{20} = +8.7°$ (c=1.10, DMF).
UV Spectrum $\lambda_{max}^{MeOH}$ 253 nm ($\epsilon$14,800).
IR Spectrum (KBr) cm$^{-1}$: 3450, 3190, 2950, 2760, 1055, 1642, 1605, 1539, 1648, 1406, 1391, 1362, 1327, 1177, 1069, 1045, 782, 685, 640.

| $^1$H-NMR Spectrum (DMSO-d$_6$) δ | |
|---|---|
| 10.82 (1H, br s, NH-1) | 4.42 (1H, m, H-2') |
| 7.83 (1H, s, H-8) | 4.03 (1H, m, H-4') |
| 6.64 (2H, s, NH$_2$-2) | 3.61 (1H, m, H-5') |
| 5.86 (1H, d, H-1') | 3.54 (1H, m, H-3') |
| 5.39 (1H, br d, OH-2') | 2.28 (1H, m, H-3') |
| 5.06 (1H, br t, OH-5') | 1.96 (1H, m, H-3'') |

EXAMPLE 24

Synthesis of 9-(3-deoxy-β-D-threo-pentofuranosyl) adenine (Compound A'3)

Adenosine (5.0 g, 18.7 mmol) was suspended in dry pyridine (50 ml) and colled to −15° C. To the suspension was added pivaloyl chloride (7.0 ml, 56.8 mmol), and the mixture was first stirred at −15° C. for 1.5 hour, and then at 0° C. for 2 hours. Methanesulfonyl chloride (4.3 ml, 55.6 mmol) was added dropwise to the reaction mixture under ice cooling. The mixture was stirred at room temperature for 3 hours, the cooled with ice again. A small amount of water was added and stirred for 30 minutes. The reaction mixture was extracted with chloroform-ether. The organic layer was washed with saturated aqueous sodium bicarbonate solution and then with water, and dried over magnesium sulfate. The drying agent was removed by filtration and the filtrate was concentrated in vacuo to dryness to give amorphous substances. The remaining pyridine was removed by repeated co-evaporation with toluene. The residue was dissolved in methanol (150 ml), cooled to −15° C., after which sodium methoxide (8.1 g, 150 mmol) and sodium borohydride (2.5 g, 66.1 mmol) were added. The mixture was first stirred at room temperature for 14 hours and then at 50° C. for 3 hours. After ice cooling, a small amount of acetone was added to the reaction mixture to decompose an excess of NaBH4. Concentrated hydrochloric acid was gradually added to neutralize the solution. Ethanol was added to the mixture, which was then concentrated under reduced pressure to remove water completely. The residue was suspended in chloroform-methanol and applied to a silica gel column (250 g). Elution with chloroform - methanol (8:1→5:1) gave compound A'3 as oils, which were then crystallized from ethanol-ether. Yield: 2.7 g (57%).

The physical properties of the product was identical with those reported earlier [R. Mengel and H. Wiedner, Chem. Ber., 109, 1395 (1976); A. Nilass and J. Chattopadhyaya, Synthesis, 1986, 196)].

PHYSICAL PROPERTIES OF COMPOUND A'3

Melting point: 190°-192° C.

| Elementary analysis | | | |
|---|---|---|---|
| | C | H | N |
| Calculated (%) (for $C_{10}H_{13}N_5O_3 \cdot 0.1H_2O$) | 47.47 | 5.26 | 27.68 |
| Found (%) | 47.36 | 5.22 | 27.67 |

Specific rotations: $[\alpha]_D^{20} = -24.3°$ (c=1.08, DMF).
UV Spectrum $\lambda_{max}^{MeOH}$ 259 nm ($\epsilon$14,200).
IR Spectrum (KBr) cm$^{-1}$: 3370, 3230, 1680, 1672, 1611, 1575, 1490, 1428, 1385, 1341, 1316, 1220, 1115, 1105, 1093, 1056, 999, 799, 721, 652, 590.

| $^1$H-NMR Spectrum (DMSO-d$_6$) δ | |
|---|---|
| 8.30 (1H, s, H-8) | 4.51 (1H, m, H-2') |
| 8.14 (1H, s, H-2) | 4.09 (1H, m, H-4') |
| 7.24 (2H, bs, NH$_2$) | 3.66 (1H, m, H-5') |
| 6.15 (1H, d, H-1') | 3.58 (1H, m, H-5'') |
| 5.42 (1H, d, OH-2') | 2.29 (1H, m, H-3') |
| 5.17 (1H, t, OH-5') | 2.02 (1H, m, H-3'') |

INDUSTRIAL UTILITY

The dideoxynucleoside derivatives among the novel nucleoside derivatives of the present invention are useful as an antiviral agent.

Those except for the dideoxynucleoside derivatives among the novel nucleoside derivatives of the present invention are useful as intermediates for synthesizing the dideoxynucleosides derivatives.

Further, according to the synthetic processes of the present invention, above-mentioned and known intermediates can be synthesized short-step reactions using inexpensive reagents.

We claim:

1. The compound 2'-3'-dideoxy-2'-azido-adenosine having the formula

2. The compound 5'-O-dimethoxytrityl-2',3'-dideoxy-2'-azido-N6-dimethoxytrityl-adenosine having the formula

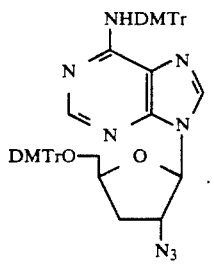
3. The compound 5'-O-dimethoxytrityl-2',3'-dideoxy-2'-iodo-N6-dimethoxytrityl-adenosine having the formula
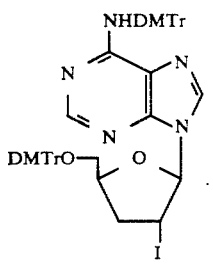
* * * * *